United States Patent
Sato et al.

(10) Patent No.: US 8,434,868 B2
(45) Date of Patent: May 7, 2013

(54) EYE-GAZE TRACKING DEVICE, EYE-GAZE TRACKING METHOD, ELECTRO-OCULOGRAPHY MEASURING DEVICE, WEARABLE CAMERA, HEAD-MOUNTED DISPLAY, ELECTRONIC EYEGLASSES, AND OPHTHALMOLOGICAL DIAGNOSIS DEVICE

(75) Inventors: Daisuke Sato, Osaka (JP); Toshiyasu Sugio, Osaka (JP)

(73) Assignee: Panasonic Corporation, Osaka (JP)

( * ) Notice: Subject to any disclaimer, the term of this patent is extended or adjusted under 35 U.S.C. 154(b) by 311 days.

(21) Appl. No.: 12/948,145

(22) Filed: Nov. 17, 2010

(65) Prior Publication Data

US 2011/0170067 A1 Jul. 14, 2011

(30) Foreign Application Priority Data

Nov. 18, 2009 (JP) ................................. 2009-262680

(51) Int. Cl.
*A61B 3/14* (2006.01)
*A61B 3/00* (2006.01)
*A61B 3/10* (2006.01)

(52) U.S. Cl.
USPC ............ 351/209; 351/200; 351/205; 351/221

(58) Field of Classification Search .................. 351/209, 351/200, 205, 105, 243, 221, 222, 246
See application file for complete search history.

(56) References Cited

U.S. PATENT DOCUMENTS

| | | | | |
|---|---|---|---|---|
| 4,950,069 A | * | 8/1990 | Hutchinson | 351/210 |
| 5,070,883 A | * | 12/1991 | Kasahara | 600/558 |
| 2005/0047629 A1 | * | 3/2005 | Farrell et al. | 382/117 |
| 2008/0188777 A1 | * | 8/2008 | Bedziouk et al. | 600/595 |
| 2009/0214485 A1 | * | 8/2009 | Gavrilova et al. | 424/93.7 |
| 2010/0309432 A1 | * | 12/2010 | Suzuki et al. | 351/210 |

FOREIGN PATENT DOCUMENTS

JP 2007-252879 10/2007

OTHER PUBLICATIONS

Nobuyuki Itsuki et al., "A Battery Model of the Eyeball to Calculate Standing Potential of the Eye", Journal of Japanese Ophthalmological Society, vol. 99, No. 9, pp. 1012-1016, Sep. 10, 1995 (with English translation).
Motohiro Mizooh, "Eyeball Position Measuring System Based on Multipoint Electro-oculography", the University of Electro-Communications masters thesis, Mar. 10, 2006 (with English translation).
Hiroyuki Manabe et al., "Full-time Wearable Headphone-Type Gaze Detector", Journal of Information Processing, Mar. 2, 2006, vol. 2006, pp. 4, 23 and 24 (with English translation).
Hiroyuki Manabe et al., "Full-time Wearable Headphone-Type Gaze Detector", CHI 2006, Work-in-Progress, Apr. 22, 2006, pp. 1073-1078.

* cited by examiner

*Primary Examiner* — Dawayne A Pinkney
(74) *Attorney, Agent, or Firm* — Wenderoth, Lind & Ponack, L.L.P.

(57) ABSTRACT

An eye-gaze tracking device, which detects a gaze direction of a user based on an electro-oculogram, includes: a drift estimating unit which estimates drift noise included in a set of observation voltages among observation voltages that are electro-oculograms generated in a living body and observed at the plurality of electrodes, based on a component outside an electro-oculography subspace that is an assembly of sets of electro-oculograms theoretically observed at a plurality of electrodes; and an eye-gaze tracking unit which detects the gaze direction of the user, based on a signal generated by removing, from the observation voltages, the drift noise estimated by the drift estimating unit.

19 Claims, 25 Drawing Sheets

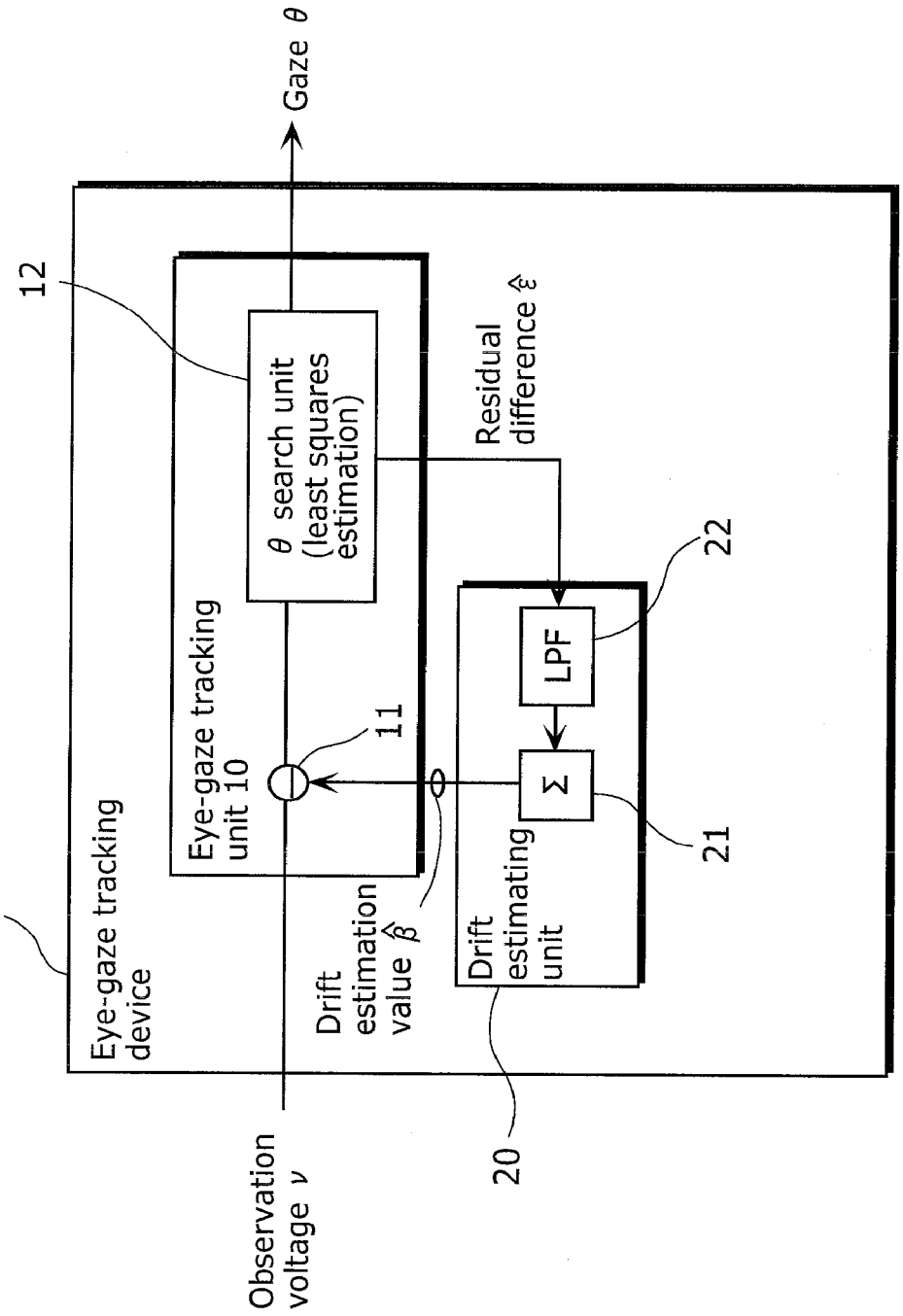

EYE-GAZE TRACKING DEVICE, EYE-GAZE TRACKING METHOD, ELECTRO-OCULOGRAPHY MEASURING DEVICE, WEARABLE CAMERA, HEAD-MOUNTED DISPLAY, ELECTRONIC EYEGLASSES, AND OPHTHALMOLOGICAL DIAGNOSIS DEVICE

BACKGROUND OF THE INVENTION (1) Field of the Invention

The present invention relates to an eye-gaze tracking device, an eye-gaze tracking method, an electro-oculography measuring device, a wearable camera, a head-mounted display, electronic eyeglasses, and an ophthalmological diagnosis device.

(2) Description of the Related Art

Conventionally, an eye-gaze tracking technique using Electro-oculography (EOG) is well known. The technique is to detect an eye-gaze by measuring eye potential (electro-oculogram) generated by a positive charge in a cornea and a negative charge in a retina, using a plurality of electrodes attached around eyes. Unlike an eye-gaze tracking technique for capturing an image of an eyeball using a camera, this technique using EOG has such advantages as not interfering with vision, not being influenced by outside light, not depending on a shape and an opening state of the eye, and achieving low power consumption, and thus is expected to be applied to various devices.

However, as shown in a waveform example (an example of three electrodes) in FIG. 1, since a low frequency noise (scores of mV) that is 100 or more times the electro-oculogram (hundreds of uV, an extended portion in FIG. 1) is mixed into the observation voltage, and an electro-oculography base line (DC) fluctuates (drifts), the observation voltage exceeds an electro-oculography range within approximately one minute, thus disabling gaze detection. In addition, the frequency range overlaps with the electro-oculogram, and it is not possible to perform frequency separation.

There are two major methods for correcting a drift as below.

<Conventional Method (1): Eye-Gaze Estimation Using an Eyeball Battery Model>

First, there is an eye-gaze tracking method (Patent Reference 1 and Non-Patent Reference 2) using a model which resembles a battery as an eyeball (Non-Patent Reference 1). Conventionally, the relationship between an eye gaze and EOG has been linearly approximated, but accuracy in gaze detection has been low due to the fact that a larger gaze angle results in greater nonlinearity. Thus, as an FOG nonlinear model, Non-Patent Reference 1 suggests a model (battery model), which assumes a cornea of an eyeball as a plus battery and a retina as a minus battery, and assumes eyeball movement as a rotation of batteries. When r and r' represent distances from the respective electrodes to a cornea center and a retina center, I is a current flowing from the retina to cornea within the eyeball, and δ is conductivity around the eyeballs, potential v generated at the electrode is calculated in accordance with (Expression 1) below:

[Math. 1]

$$v = \frac{I}{4\pi\sigma}\left(\frac{1}{r} - \frac{1}{r'}\right) \quad \text{(Expression 1)}$$

Patent Reference 1 and Non-Patent Reference 2 assume that a drift is caused by a temporal fluctuation of the current I, and also estimate, by EM algorithm, a gaze position and the current I such that a least square error between the observation voltage and a theoretical voltage calculated using the battery model is smallest.

<Conventional Method (2): Eye-Gaze Estimation Using Kalman Filter>

For another conventional method, there is a method using Kalman filter (Non-Patent References 3 and 4). An EOG(t) measured from a pair of electrodes is modeled as shown in (Expression 2A) and (Expression 2B) below, using: a two-dimensional vector x(t) which represents a gaze direction; a conversion matrix Z for converting the gaze direction into EOG; and a noise component e(t) including a DC offset and a drift:

[Math 2]

$$EOG(t) = Z \cdot x(t) + e(t) \quad \text{(Expression 2A)}$$

$$\Delta EOG(t) = Z \cdot \Delta x(t) + \Delta e(t) \quad \text{(Observation equation) (Expression 2B)}$$

In addition, movement of the gaze is modeled using a state transition matrix F(t) and a state estimation error w(t), as shown in (Expression 3) below, and is predicted as shown by:

[Math 3]

$$\Delta x(t+1) = F(t) \cdot \Delta x(t) + w(t) \quad \text{(State equation) (Expression 3)}$$

By solving these observation equation and state equation by Kalman filter, the gaze direction x(t) is estimated.

In addition, it is possible to respond to both problems of variation in drift amount that varies between each electrode, and of signal abnormality occurring at a particular electrode (due to falling of the electrode or change in contact state) by appropriately applying a covariance matrix Δe(t); thus, a robust eye-gaze estimation is performed by assuming, as noise, the signal generated by subtracting the EOG component involved in eyeball movement from the observation value, and updating the covariance matrix Δe(t).

[Patent Reference]

[Patent Reference]

[Patent Reference 1] Japanese Unexamined Patent Application Publication 2007-252879

[Non-Patent Reference]

[Non-Patent Reference 1] Itsuki, et. Al "A Battery Model of the Eyeball to Calculate Standing Potential of the Eye", Journal of Japanese Ophthalmological Society Vol. 99, No. 9, pp. 1012-1016, Sep. 10, 1995

[Non-Patent Reference 2] Mizoo, Advisor: Sakaguchi, "Eyeball Position Measuring System Based on Multipoint Electro-oculography", the University of Electro-Communications masters thesis.

[Non-Patent Reference 3] Manabe, Fukumoto, "Full-time Wearable Headphone-type Gaze Detector" (in Japanese), Journal of Information Processing, Mar. 2, 2006, Vol. 2006, page 4, 23-24.

[Non-Patent Reference 4] H. Manabe, M. Fukumoto, "Full-time Wearable Headphone-type Gaze Detector", CHI2006, Work-in-Progress, pp. 1073-1078.

However, the conventional technique (1) described above (battery model method) has considered that the drift is caused by amplitude fluctuation in EOG due to change in current I in (Expression 1). Evidently, EOG has characteristics that amplitude fluctuates due to change in amount of light incident on eyes (in ophthalmology, Arden ratio (EOG amplitude ratio between light and dark environment) is used as a test item), but a dominant cause of a drift is a baseline drift in EOG (DC variation) caused by biophysiological change, body motion, contact stability of the electrode, polarization at the electrode, and so on which occur even in an environment without light-dark fluctuations, and corresponds to the fluctuation in an offset term e(t) in (Expression 2) according to the conventional method (2). In other words, the conventional method (1) does not correct the drift of the baseline e(t) in EOG.

In addition, the conventional method (2) (Kalman filter method) does not describe the detail, but normally, Kalman filter assumes Gaussianity (normal distribution) of noise, and particularly is based on a premise that a noise distribution mean does not fluctuate. However, the drift, even when differentiated as shown in (Expression 3), is noise having a sharply-fluctuating mean value, and thus significantly deteriorating accuracy in estimating the gaze direction. That is, only predicting gaze movement is not sufficient, and gaze accuracy significantly deteriorates without estimation of the drift (especially, a mean value). In addition, although the relationship between the gaze and the electro-oculogram is linearly approximated using the conversion matrix Z, the closer the electrode is to the eyeball, the greater nonlinearity becomes, thus causing another problem of errors and deterioration in accuracy.

SUMMARY OF THE INVENTION

As described above, the conventional configuration has low accuracy in drift correction, which causes a problem of low accuracy in gaze detection. The present invention is to solve such a problem, and it is an object of the present invention to provide a eye-gaze tracking device which can estimate a gaze direction of a user with high accuracy, by estimating a drift with high accuracy.

An eye-gaze tracking device according to an aspect of the present invention is an eye-gaze tracking device which detects a gaze direction of a user based on an electro-oculogram, and the eye-gaze tracking device includes: a drift estimating unit which estimates drift noise included in a set of observation voltages among observation voltages that are electro-oculograms generated in a living body and observed at the plurality of electrodes, based on a component outside an electro-oculography subspace that is an assembly of sets of electro-oculograms theoretically observed at a plurality of electrodes; and an eye-gaze tracking unit which detects the gaze direction of the user, based on a signal generated by removing, from the observation voltages, the drift noise estimated by the drift estimating unit.

Here, the "electro-oculography subspace" may be calibrated in advance or may be dynamically estimated.

This eye-gaze tracking device can measure an electro-oculogram with high accuracy by estimating a drift, using a component which is present outside the electro-oculography subspace and can be determined as a drift amount.

Preferably, the electro-oculography subspace is obtained by mapping a point in a gaze vector space in accordance with a predetermined electro-oculography conversion function, the point indicating the gaze direction of the user within a predetermined range.

Here, the "predetermined range" is a range of a possible value of the gaze, and may be, for example: a horizontal gaze angel within ±50°, a vertical gaze angle from −50° or more to 30° or less, and a vergence angle of 20° or less, and so on.

In addition, the "predetermined electro-oculography conversion function" is a function to convert the gaze direction (a point in a gaze vector space indicating the gaze direction), into electro-oculogram, and the gaze direction may be calculated by calibration or may be dynamically estimated. Note that the electro-oculography conversion function may be linear or nonlinear. The function, when it is linear, allows expression in a matrix.

Normally, the electro-oculogram is hundreds of uV or so, but the drift has an amplitude of scores of mV order that is 100 times or higher than the normal electro-oculogram. By setting the eyeball range of motion (predetermined range), it is possible to significantly reduce the drift to a hundredth or less (equal to or below the electro-oculography range).

In addition, a boundary of the predetermined range may be a curve.

Here, the "curve", for example, is an ellipse. By representing the eyeball range of motion in the curve, it is possible to further increase accuracy in separating the drift from the electro-oculogram.

In addition, the boundary of the predetermined range may be a curve which is vertically asymmetrical with respect to a horizontal gaze direction of the user.

Normally, an upper portion of a human eyeball has a narrower range of motion than that of a lower portion. Thus, by limiting an upper range, it is possible to further increase accuracy in separating the drift from the electro-oculogram.

In addition, the predetermined range may be a range of the gaze direction of the user when the user circularly rotates an eyeball.

For example, the eyeball is rotated by 360 degrees in a large circular motion up to a limit. With this, it is possible to easily measure an eyeball motion limit (range of the user's gaze direction). Note that being "circular" need not be a precise circle but is a curve different from user to user.

In addition, the eye-gaze tracking device described above may further include a function calculating unit which calculates the electro-oculography conversion function based on an observation voltage observed at each of the plurality of electrodes for each gaze direction, and the function calculating unit may estimate the drift noise based on a difference between two observation voltages that are observed at a same point when the user circularly rotates the eyeball two times, and may calculate the electro-oculography conversion function based on a voltage obtained by removing the estimated drift noise from at least one of the two observation voltages.

For example, when circularly rotating the eyeball by 360 degrees, by recording a voltage at a start point and a voltage at an end point and interpolating these points, the drift noise during the calibration is estimated so as to be removed from the observation voltage, thus allowing calculating the electro-oculography conversion function with high accuracy without being affected by the drift noise.

Note that the same point need not be completely "the same" but may be more or less different.

In addition, the electro-oculography conversion function may be a nonlinear function.

Although depending on where to attach the electrodes, in the linear model, a larger gaze angle results in a larger error of the electro-oculography conversion function (approximately 5° to 10°), thus deteriorating drift estimation accuracy (drift noise estimation accuracy) and gaze direction estimation accuracy. Particularly, in the feedback configuration described later, a linear approximation error is accumulated as a drift estimation error. This configuration, due to the highly-accurate electro-oculography conversion function that considers nonlinearity of electro-oculograms, allows highly accurate electro-oculography measurement and gaze detection.

In addition, the nonlinear function may be a function for calculating a theoretical value of the electro-oculogram generated at an arbitrary three-dimensional spatial position, based on: a right-eye corneal distance and a right-eye retinal distance each of which is a distance to the arbitrary three-dimensional spatial position from a corresponding one of a right eye cornea and a right eye retina; and a left-eye corneal distance and a left-eye retinal distance each of which is a distance to the arbitrary three-dimensional spatial position from a corresponding one of a left eye cornea and a left eye retina.

Here, the "arbitrary three-dimensional spatial position" is a surface, an interior, and so on of the living body. This configuration, although mainly intended to calculate a theoretical value of electro-oculogram generated in the electrodes attached to the skin of the living body, is not limited to this example.

This electro-oculography estimating device is a model to calculate with accuracy, as a specific model of the "influence of crosstalk caused by the other eye", a theoretical value of the electro-oculogram generated in the arbitrary three-dimensional spatial position, using a function in accordance with a distance from the cornea and retina of each eye. In addition, since the device allows calculating electro-oculogram with high accuracy even in a region having a large amount of crosstalk (near a binocular center), a nose-pad portion of the eyeglasses may include an electrode, thereby allowing increasing freedom in attachment position of the electrodes. In addition, it is also possible to calculate three-dimensional coordinates of the gaze point, and also allows distance measuring, thus various applications can be expected.

In addition, the nonlinear function may include predetermined coefficients each of which is individually settable for a corresponding one of the right-eye corneal distance, the right-eye retinal distance, the left-eye corneal distance, and the left-eye retinal distance.

In this eye-gaze tracking device, as a specific model of the "consideration of an influence of the tissue around the eyeball and so on", the influences of elements such as bones, muscles, and cells are modeled by assuming the interior of the head region as a non-uniform permittivity space and assuming each of the predetermined coefficients as settable for a corresponding one of the right-eye corneal distance, right-eye retinal distance, left-eye corneal distance, and left-eye retinal distance. This allows calculating electro-oculogram with high accuracy.

Here the "predetermined coefficient" is a value corresponding to a charge amount, permittivity, current density, and conductivity, and so on.

Note that a three-dimensional distribution of the permittivity space may be held in a three-dimensional lookup table or the like after dividing the intra-head model into subregions.

In addition, the function calculating unit may calculate the nonlinear function by interpolating the electro-oculogram in a gaze direction in which no voltage is observed, using each of the observation voltages observed at each of the plurality of electrodes for each gaze direction.

This allows reducing circuit scale or an amount of calculation for preparing the electro-oculography conversion function.

In addition, when, at time t, N observation voltages are $V_i(t)$ (i=1, ..., N), and a drift estimation value of the drift noise included in each of the N observation voltages is $$\hat{\beta}_i(t) \qquad \text{[Math 4]}$$

and when the electro-oculography conversion function corresponding to each of the N observation voltages is $eog_i(\ )$, and the gaze position of the user is $\theta(t)$, the eye-gaze tracking unit may estimate, so as to derive a smallest value in accordance with $$\sum_{i=1}^{N} \left( v_i(t) - \left( eog_i(\theta(t)) + \hat{\beta}_i(t) \right) \right)^2, \qquad \text{[Math 5]}$$

a gaze estimation value $$\hat{\theta}(t) \qquad \text{[Math 6]}$$

which is an estimation value of the gaze position $\theta(t)$ of the user, and when a residual difference at the time of estimating the gaze estimation value detected by the eye-gaze tracking unit is $$\hat{\epsilon}_i(t) = v_i(t) - (eog_i(\theta(t)) + \hat{\beta}_i(t)) \qquad \text{[Math 7]}$$

the drift estimating unit may estimate the drift estimation value in accordance with:

$$\hat{\beta}_i(t) = \hat{\beta}_i(t-\Delta t) + \hat{\epsilon}_i(t-\Delta t) \qquad \text{[Math 8]}$$

According to this configuration, the observation voltage is suppressed within the electro-oculography subspace by continuously removing the drift estimation value by feedback control. This allows removing the drift.

In addition, the drift estimating unit may perform low-pass filtering on the residual difference, and may estimate the drift estimation value from the residual difference on which the low-pass filtering has been performed.

In some cases, the residual error includes a high-frequency noise, and causes deterioration in accuracy when the high-frequency noise is fed back to the observation voltage. Thus, by removing the high-frequency noise from the residual error using a low-pass filter, it is possible to remove the drift noise with higher accuracy.

In addition, the drift estimating unit may increase a cutoff frequency for the low-pass filtering when the gaze estimation value exceeds the boundary of the predetermined range.

In other words, in the case of the observation voltage below the electro-oculography range (when a gaze estimation value is within a predetermined range), a calibration speed is reduced in consideration of a calibration error of electro-oculography by assuming, for example, that the cutoff frequency fc=1 Hz, and it is possible to increase correction responsiveness by assuming that fc=5 Hz in the case of the observation voltage equal to or above the electro-oculography range (when the gaze estimation value exceeds a boundary of the predetermined range).

In addition, the eye-gaze tracking device described above may further include a saccade detecting unit which detects, from the observation voltages, an occurrence of saccadic movement that is rapid eyeball movement, and the drift estimating unit may decrease the cutoff frequency for the low-pass filtering when the saccade detecting unit detects the occurrence of the saccadic movement.

When simply using a low-pass filter, low-pass filtering is performed even when not only a high-frequency noise but a high-frequency eyeball movement (saccadic movement=saccadic eye movement) is generated, thus causing deterioration in drift correction responsiveness. Thus, the low-pass filter may be adaptively weakened by lowering the cutoff frequency during saccadic movement.

In addition, the saccade detecting unit may include: a delayed signal generating unit which outputs a delayed signal by delaying each of the observation voltages for a predetermined delay time; and a subtraction unit which generates an output signal by subtracting the delayed signal from the each of the observation voltages, and the saccade detecting unit may determine a signal above a predetermined threshold as a saccade signal indicating saccadic movement, the signal being included in the output signal, and the predetermined delay time may be shorter than a single fixation time of the user.

An eye-gaze tracking method according to another aspect of the present invention is an eye-gaze tracking method for detecting a gaze direction of a user based on an electro-oculogram, and the eye-gaze tracking method includes: estimating drift noise included in a set of observation voltages among the observation voltages that are the lo electro-oculograms generated in a living body and observed at the plurality of electrodes, based on a component outside an electro-oculography subspace that is an assembly of sets of electro-oculograms theoretically observed at a plurality of electrodes; and detecting the gaze direction of the user, based on a signal generated by removing, from the observation voltages, the drift noise estimated in the estimating.

An electro-oculography measuring device according to yet another aspect of the present invention is an electro-oculography measuring device which measures an electro-oculogram of a user, and the electro-oculography measuring device includes: a drift estimating unit which estimates drift noise included in a set of observation voltages, based on a component outside an electro-oculography subspace that is an assembly of sets of electro-oculograms theoretically observed at a plurality of electrodes, the observation voltages being electro-oculograms generated in a living body and observed at the plurality of electrodes; and a subtractor which subtracts the drift noise estimated by the drift estimating device, based on the observation voltages.

A wearable camera according to yet another aspect of the present invention is a wearable camera which captures an image in a gaze direction of a user, and the wearable camera includes: an imaging unit; the eye-gaze tracking device described above; and the imaging control unit which causes the imaging unit to capture the image in the gaze direction detected by the eye-gaze tracking device.

A head-mounted display according to yet another aspect of the present invention is a head-mounted display which moves a mouse pointer in a gaze direction of a user, and the head-mounted display includes: a display unit which displays an image and the mouse pointer; the eye-gaze tracking device described above; and a display control unit which moves the mouse pointer in the gaze direction detected by the eye-gaze tracking device, the mouse pointer being displayed on the display unit.

Electronic eyeglasses according to yet another aspect of the present invention are electronic eyeglasses which change a focal point of each of lenses according to a gaze position of a user, and the electronic eyeglasses include: lenses each having a changeable focal point; the eye-gaze tracking device described above; and a focus control unit which changes the focal point of each of the lenses according to the gaze position detected by the eye-gaze tracking device.

An ophthalmological diagnosis device according to yet another aspect of the present invention is an ophthalmological diagnosis device which diagnoses a retinal state of a user, and the ophthalmological diagnosis device includes: the eye-gaze tracking device described above; and a diagnosis unit which detects retinal abnormality of the user, based on the signal obtained by removing, from the observation voltages, the drift noise estimated by the drift estimating unit.

A program according to yet another aspect of the present invention is a program for detecting a gaze direction of a user based on an electro-oculogram, and the program causes a computer to execute: estimating drift noise included in a set of observation voltages among the observation voltages that are the electro-oculograms generated in a living body and observed at the plurality of electrodes, based on a component outside an electro-oculography subspace that is an assembly of sets of electro-oculograms theoretically observed at a plurality of electrodes; and detecting the gaze direction of the user, based on a signal generated by removing, from the observation voltages, the drift noise estimated in the estimating.

With the eye-gaze tracking device according to the present invention, it is possible to detect the gaze direction of the user with high accuracy, by estimating a drift with high accuracy.

FURTHER INFORMATION ABOUT TECHNICAL BACKGROUND TO THIS APPLICATION

The disclosure of Japanese Patent Application No. 2009-262680 filed on Nov. 18, 2009 including specification, drawings and claims is incorporated herein by reference in its entirety.

BRIEF DESCRIPTION OF THE DRAWINGS

These and other objects, advantages and features of the invention will become apparent from the following description thereof taken in conjunction with the accompanying drawings that illustrate a specific embodiment of the invention. In the Drawings:

FIG. 28 is a block diagram showing essential constituent elements of the eye-gaze tracking device according to the present invention.

DESCRIPTION OF THE PREFERRED EMBODIMENTS

Figure 1:
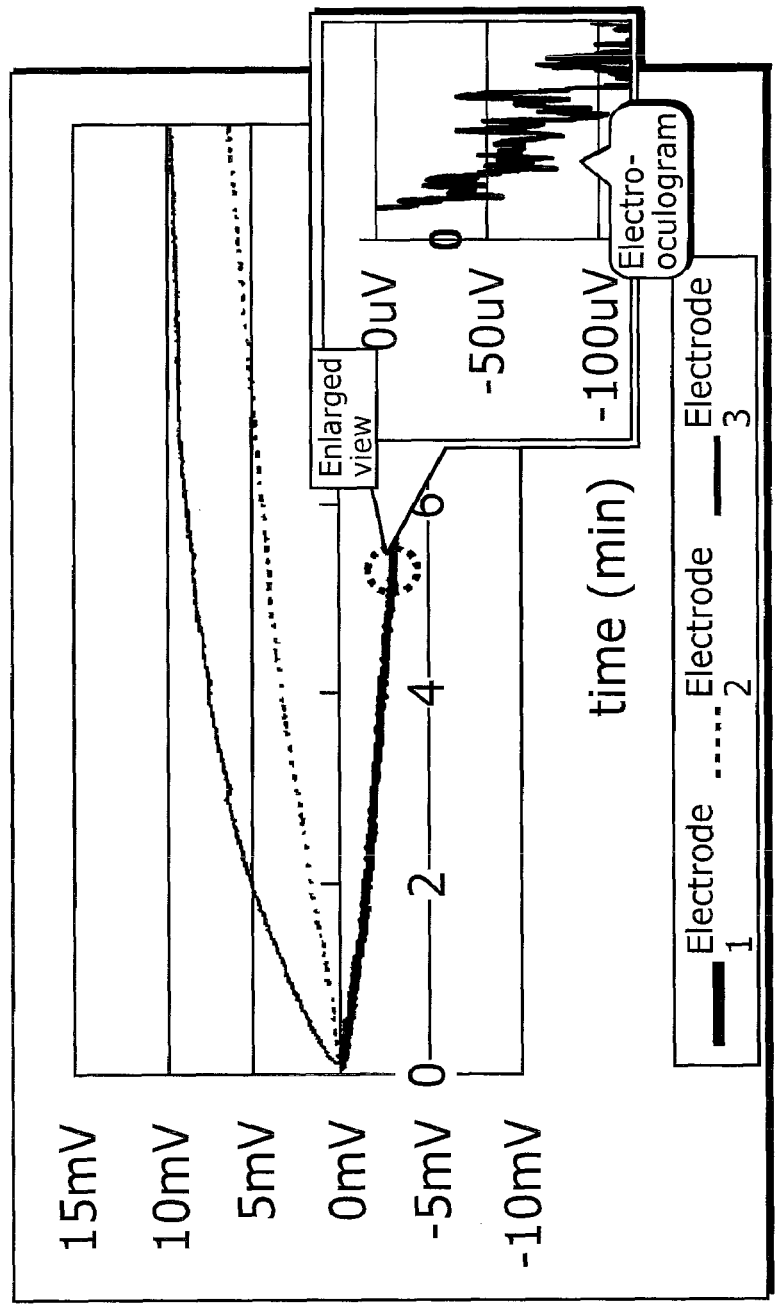
FIG. 1 is a graph of an example of an observation voltage waveform.

Hereinafter, an eye-gaze tracking device according to embodiments of the present invention will be described with reference to the drawings.

(First Embodiment)

An eye-gaze tracking device according to a first embodiment of the present invention will be described with reference to FIGS. 2 to 17.

<Model>

Observation voltage v(t) at time t is modeled as shown in (Expression 4) below, using: a gaze position θ(t); an electro-oculography conversion function eog( ) for converting the gaze into electro-oculogram; and noise e(t) (=a drift β(t)+a normal distribution noise n(t)). Here, the normal distribution noise n(t) includes: a high-frequency noise, a gaze estimation error, and a drift estimation error, or the like.

[Math 9]

$$v(t) = eog(\theta(t)) + e(t) = eog(\theta(t)) + \beta(t) + n(t) \quad \text{(Expression 4)}$$

Of these, the electro-oculography conversion function eog( ) is modeled by calibration, using $$\hat{\beta}(t) \quad \text{[Math 10]}$$

which is a drift estimation value estimated as drift β(t) by the estimation method described later, and using, as the normal distribution noise n(t), a squared differences sum function (the number of voltages N) that is a log likelihood function in normal distribution. In other words, a gaze estimation value $$\hat{\theta}(t) \quad \text{[Math 11]}$$

which is an estimation value of the gaze position is estimated in accordance with (Expression 5) below:

[Math 12]

$$\hat{\theta}(t) = \operatorname*{argmin}_{\theta \in \Theta} \sum_{i=1}^{N} \left( v_i(t) - \left( eog_i(\theta(t)) + \hat{\beta}_i(t) \right) \right)^2 \quad \text{(Expression 5)}$$

Here, it is assumed that: the N observation voltages at time t is $v_i(t)$ (i=1, ..., N), and a drift estimation value that is an estimation value of the drift noise included in each observation voltage is $$\hat{\beta}_i(t) \quad \text{[Math 13]}$$

and the electro-oculography conversion function corresponding to each observation voltage is $eog_i(\ )$.

Note that according to the present embodiment, for simplicity, the electro-oculography conversion function eog( ) is estimated by calibration based on an assumption that a temporal change in EOG amplitude is not caused by an amount of incident light on the retina, but the estimation may be performed using a signal (variance change in observation potential or the like) or may be performed by providing a brightness sensor (camera and so on) or the like in consideration of change in light amount.

In addition, as the method of searching for a least squares solution, any method may be used such as: a nonlinear optimization technique (including the gradient descent method and the Levenberg-Marquardt method); full search (performing a full search based on a predetermined granularity by setting a search range Θ of θ); and a nonlinear Kalman filter, the Monte Carlo filter. In addition, the solution need not be strictly the "least", but may be a neighborhood value.

The following will describe the method of calibration using the electro-oculography conversion function eog( ), a drift estimating method, and an eye-gaze tracking method.

<Electro-Oculography Conversion Function Calibration>

First, the method of calibrating the electro-oculography conversion function eog( ) will be described with reference to FIGS. 2 to 7. The following will describe: an electro-oculography model based on electrophysiology in an implementation of the present invention; the method of estimating the model parameter; and an electro-oculography conversion function.

Note that the method of calibrating the electro-oculography conversion function as shown below is a mere example, and it is possible to consider other various methods including: a method of linearly approximating electro-oculogram, a method using a nonlinear function (a polynomial function equal to or higher than a second order), a method of learning the relationship between an electro-oculogram and a gaze using a neural net, or simply a method of interpolating or is extrapolating calibration data (linear interpolation or the nearest neighbor method).

<1. Electro-Oculography Model>

Figure 2:
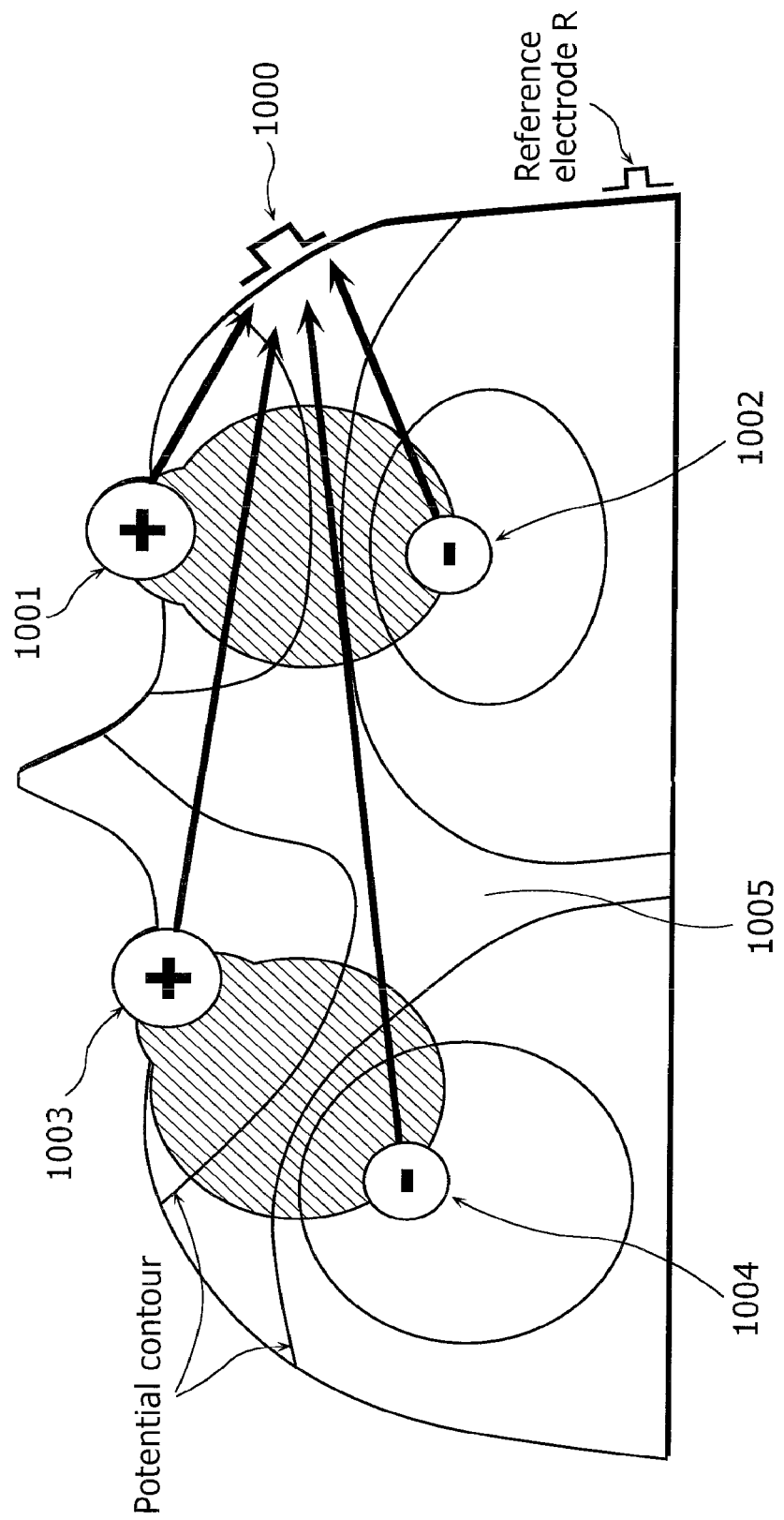
FIG. 2 is a schematic diagram showing an electro-oculography model according to the first embodiment of the present invention.

FIG. 2 is a schematic diagram showing an electro-oculography model according to a first embodiment of the present invention (a cross-sectional view of the head region as viewed from eye position). The electro-oculography model is a model for representing influences of elements such as bones, muscles, and cells within the head region as a permittivity space 1005 that is not uniform, and calculating a theoretical value of an observation potential (electro-oculography theoretical value) generated in an electrode 1000 due to a right-eye corneal charge 1001, a right-eye retinal charge 1002, a left-eye corneal charge 1003, and a left-eye retinal charge 1004.

According to this electro-oculography model, it is possible to calculate an electro-oculography theoretical value with high accuracy not only for one eye but also including a crosstalk potential from the other eye, thus allowing calculating the electro-oculography theoretical value with high accuracy. In addition, at an electrode position where a large amount of crosstalk occurs (near a binocular center), it is also possible to calculate generated potential with high accuracy, thus allowing freedom in attachment position of the electrodes as well as allowing attachment of electrodes at positions appropriate for intended use. Furthermore, the electro-oculography model considers an influence of non-uniform permittivity (or conductivity) space due to the bones, muscles, cells, and so on within the head region, it is possible to calculate the electro-oculography theoretical value with higher accuracy. Hereinafter, the processing for calculating an electro-oculography theoretical value v for a three-dimensional gaze position θ will be described.

Figure 3:
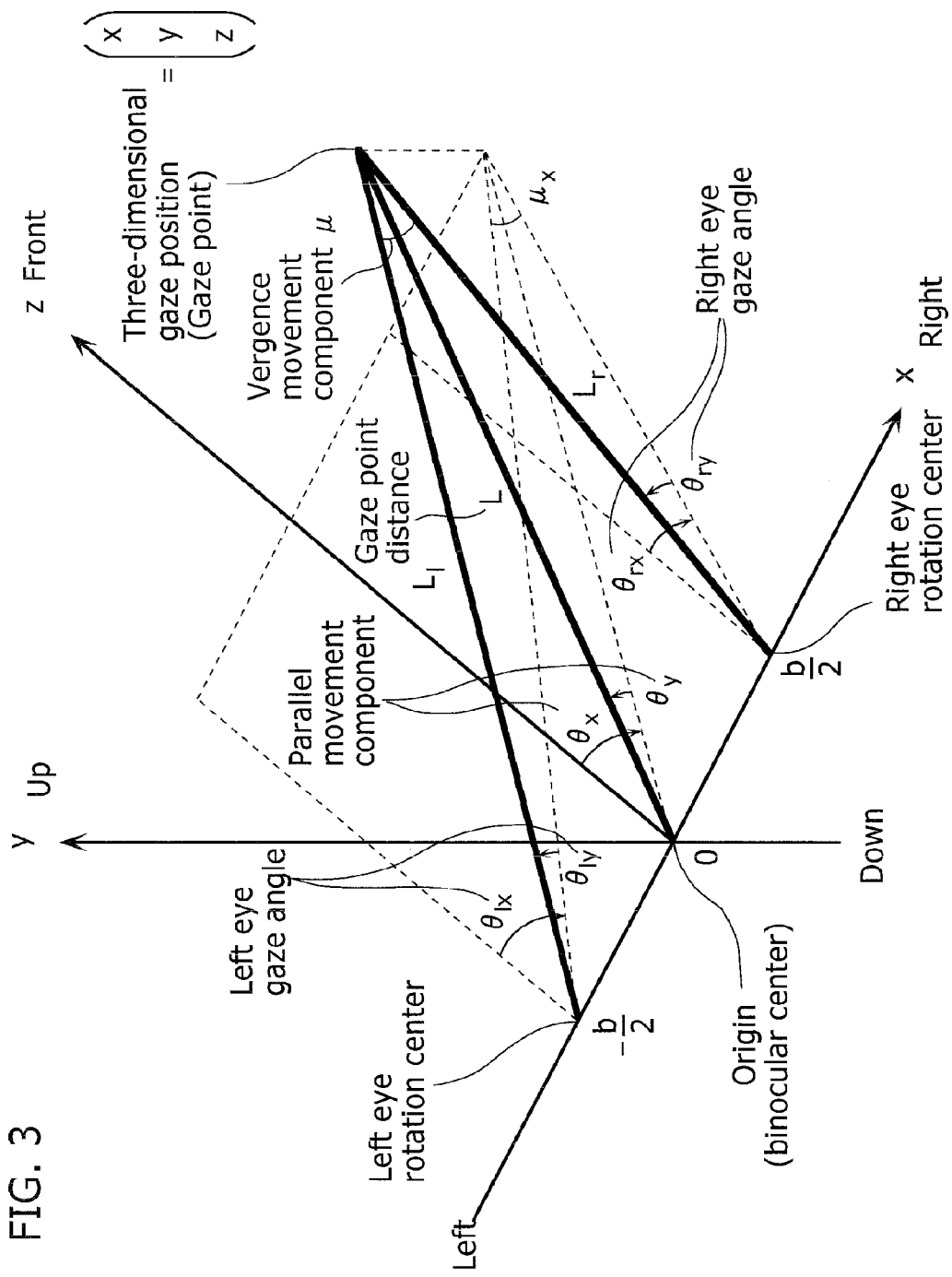
FIG. 3 is an explanatory diagram of each parameter according to the first embodiment of the present invention.

As shown in FIG. 3, it is assumed that a midpoint of a rotation center of each of the right and left eyes (binocular center point) is an origin, with an x-axis representing a rightward direction, a y-axis representing an upward direction, and a z-axis representing a forward direction. Furthermore, it is assumed that: b represents a binocular space; θ=(x, y, z) represents a three-dimensional gaze position (gaze point); ($\theta_x$, $\theta_y$) represents a parallel movement component of both eyes; μ represents a vergence movement component of both eyes; ($\theta_{rx}$, $\theta_{ry}$) represents a right-eye horizontal and vertical gaze angle; ($\theta_{lx}$, $\theta_{ly}$) represents a left-eye horizontal and vertical gaze angle; and L represents a gaze point distance. In addition, it is assumed that a represents an eyeball radius, and ($x_e$, $y_e$, $z_e$) represents electrode coordinates.

Here, $\theta_x$ of the parallel movement component of both eyes ($\theta_x$, $\theta_y$) represents degrees of an angle at which both eyes have moved in the x-axis direction from a state of looking frontward, and $\theta_y$ represents degrees of an angle at which both eyes have moved in the y-axis direction from a state of looking frontward. In other words, as shown in FIG. 3, $\theta_x$ represents an angle between the z-axis and a projection line that is a straight line connecting the binocular center point and the gaze point and projected onto an x-y plane (a plane formed by the x-axis is and y-axis). In addition, $\theta_y$ represents an angle between the projection line and a straight line connecting the binocular center point and the gaze point.

The vergence movement component μ is a component to define an angle between the gazes of both eyes when both eyes are looking inward at the same time. In other words, as shown in FIG. 3, μ represents an angle between a straight line connecting a left-eye rotation center and the gaze point, and a straight line connecting a right-eye rotation center and the gaze point.

Of the right-eye horizontal and vertical gaze angles ($\theta_{rx}$, $\theta_{ry}$), the horizontal gaze angle $\theta_{rx}$ represents degrees of an angle at which the right eye has moved in the x-axis direction from a state of looking frontward, and $\theta_{ry}$ represents degrees of an angle at which the right eye has moved in the y-axis direction from a state of looking frontward. In other words, as shown in FIG. 3, the horizontal gaze angle $\theta_{rx}$ represents an angle between the z-axis and a projection line that is a line connecting the right-eye rotation center and the gaze point and projected onto the x-y plane. In addition, $\theta_{ry}$ represents an angle between the projection line and a straight line connecting the right-eye rotation center and the gaze point.

Of the left-eye horizontal and vertical gaze angles ($\theta_{lx}$, $\theta_{ly}$), the horizontal gaze angle $\theta_{lx}$ represents degrees of an angle at which the left eye has moved in the x-axis direction from a state of looking frontward, and $\theta_{ly}$ represents degrees of an angle at which the left eye has moved in the y-axis direction from a state of looking frontward. In other words, as shown in FIG. 3, the horizontal gaze angle $\theta_{lx}$ represents an angle between the z-axis and a projection line that is a line connecting the left-eye rotation center and the gaze point and projected onto the x-y plane. In addition, $\theta_{ly}$ represents an angle between the projection line and a straight line connecting the left-eye rotation center and the gaze point.

There are various types of methods for representing the three-dimensional gaze position θ=(x, y, z); however, in the following description, the three dimensional gaze position is represented as θ=($\theta_x$, $\theta_y$, z), using the parallel movement components of both eyes and the z-coordinates of the three-dimensional gaze position (gaze point). Note that, for another method, the three-dimensional gaze position may also be represented as θ=($\theta_x$, $\theta_y$, μ), using the vergence movement component μ of both eyes. Note that according to the present embodiment both eyes are assumed as gazing at the same gaze point.

First, the model estimating unit (not shown in the figure) in the gaze tracking device calculates the horizontal and vertical gaze angle ($\theta_{rx}$, $\theta_{ry}$, $\theta_{lx}$, $\theta_{ly}$) in accordance with (Expression 6) below:

[Math 14]

$$\theta_{rx} = \tan^{-1}(\tan\theta_x - b/2z)$$

$$\theta_{lx} = \tan^{-1}(\tan\theta_x + b/2z)$$

$$\theta_{ry} = \tan^{-1}(\tan\theta_y \cos\theta_{rx}/\cos\theta_x)$$

$$\theta_{ly} = \tan^{-1}(\tan\theta_y \cos\theta_{lx}/\cos\theta_x) \quad \text{(Expression 6)}$$

Next, the distance obtaining unit calculates, in accordance with (Expression 7) below, the right-eye corneal distance $r_1$, the right-eye retinal distance $r_2$, the left-eye corneal distance $r_3$, and the left-eye retinal distance $r_4$ each of which represents a distance from each electrode to a corresponding one of the right eye cornea, the right eye retina, the left eye cornea, and the left eye retina.

[Math 15]

$$r_1 = \sqrt{(x_e - b/2 - a\cos\theta_{ly}\sin\theta_{lx})^2 + (y_e - a\sin\theta_{ly})^2 + (z_e - a\cos\theta_{ly}\cos\theta_{lx})^2}$$

$$r_2 = \sqrt{(x_e - b/2 + a\cos\theta_{ly}\sin\theta_{lx})^2 + (y_e + a\sin\theta_{ly})^2 + (z_e + a\cos\theta_{ly}\cos\theta_{lx})^2}$$

$$r_3 = \sqrt{(x_e + b/2 - a\cos\theta_{ly}\sin\theta_{lx})^2 + (y_e - a\sin\theta_{ly})^2 + (z_e - a\cos\theta_{ly}\cos\theta_{lx})^2}$$

$$r_4 = \sqrt{(x_e + b/2 + a\cos\theta_{ly}\sin\theta_{lx})^2 + (y_e + a\sin\theta_{ly})^2 + (z_e + a\cos\theta_{ly}\cos\theta_{lx})^2}$$

In addition, permittivity from the electrode to each of the right eye cornea, the right eye retina, the left eye cornea, and the left eye retina is defined as $\epsilon_1$, $\epsilon_2$, $\epsilon_3$, and $\epsilon_4$, respectively, and a charge amount of each of the right eye cornea, the right eye retina, the left eye cornea, and the left eye retina is defined as $q_1$, $q_2$, $q_3$, and $q_4$, respectively. At this time, the model estimating unit calculates an electro-oculography theoretical value $$\hat{v} \quad \text{[Math 16]}$$

in accordance with (Expression 8) below:

[Math 17]

$$\hat{v} = \frac{q_1}{4\pi\epsilon_1 r_1} + \frac{q_2}{4\pi\epsilon_2 r_2} + \frac{q_3}{4\pi\epsilon_3 r_3} + \frac{q_4}{4\pi\epsilon_4 r_4} \quad \text{(Expression 8)}$$

Figure 4:
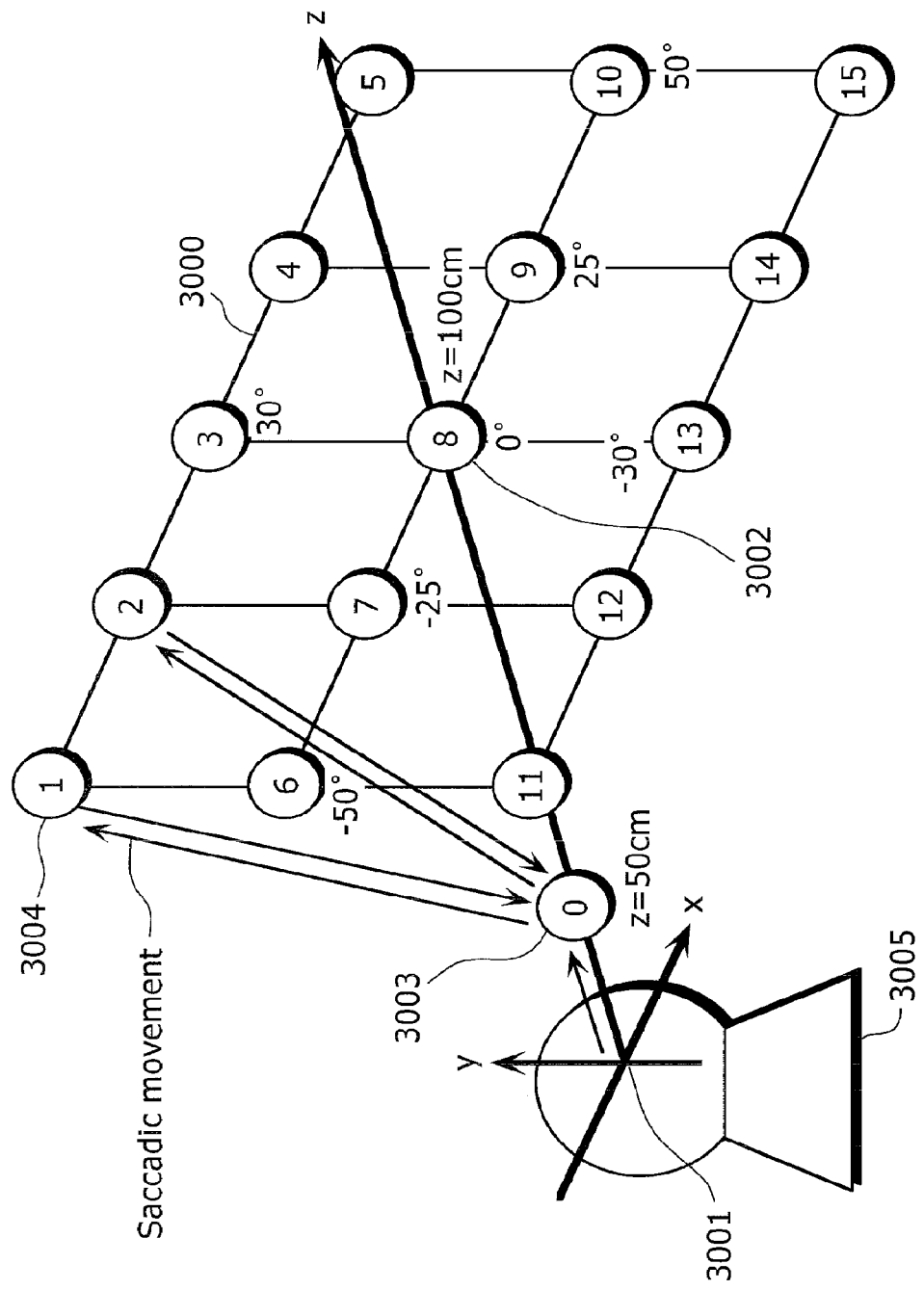
FIG. 4 is an explanatory diagram of a calibration method according to the first embodiment of the present invention.

Note that here, the electro-oculography theoretical value is calculated based on infinity as a reference potential; however, since the processing is easier when assuming, as the reference potential, the potential observed when the user is gazing at the reference index ($\theta_x=\theta_y=0$, z=a predetermined value) that is shown in FIG. 4, it is preferable to subtract the electro-oculogram at this time as an offset potential. However, the following will omit the description of the offset potential for simplicity of description.

Here, furthermore, assuming that values representing the charge amount and permittivity do not vary depending on eyeball movement, (Expression 8) is simplified as (Expression 9), using the predetermined coefficients $\alpha_1$, $\alpha_2$, $\alpha_3$, and $\alpha_4$.

[Math 18]

$$\hat{v}=\alpha_1/r_1+\alpha_2/r_2+\alpha_3/r_3+\alpha_4/r_4 \qquad \text{(Expression 9)}$$

Note that here, for simplicity of description, infinity is assumed as a reference voltage (0 V), but the model estimating unit may calculate and subtract the offset potential observed when the user is gazing frontward because the electro-oculogram when gazing at the front ($\theta_x=\theta_y=0$) is assumed as the reference voltage.

(Expression 8) or (Expression 9) is a function for calculating the theoretical value of electro-oculogram generated at the arbitrary three-dimensional position, based on the right-eye corneal distance, the right-eye retinal distance, the left-eye corneal distance, and the left-eye retinal distance. Here, the "arbitrary three-dimensional spatial position" is a surface, an interior, and so on of the living body.

<2 Model Parameter Estimation>

The following will describe calibration of unknown parameters (model parameters) of the electro-oculography model, that is: eyeball radius a, binocular space b, electrode coordinates ($x_e$, $y_e$, $z_e$), and the predetermined coefficients $\alpha_1$, $\alpha_2$, $\alpha_3$, and $\alpha_4$. Note that in the following description, assuming the eyeball radius a and the binocular space b as a=12 mm and b=65 mm, respectively, the model estimating unit estimates only the electrode coordinates ($x_e$, $y_e$, $z_e$), and the predetermined coefficients $\alpha_1$, $\alpha_2$, $\alpha_3$, and $\alpha_4$.

<2-1 Obtaining Calibration Data>

First, the model estimating unit obtains calibration data (learning data). A method of obtaining the calibration data will be described with reference to FIG. 4.

(Preparation)

A user is seated with a binocular center 3001 pointed at a center point 3002 of a monitor 3000, and gazes at a reference index 3003 (on the z-axis) provided between the user and the monitor 3000. The reference index 3003 may be anything such as substituting the user's thumb that is stood in front of the eyes, but should preferably be something that does not move.

(Obtaining Data)

(1) When a calibration index 3004 (gaze position $\theta$) is presented on the monitor 3000, the user gazes at the calibration index 3004 through saccadic movement (saccadic eye movement). At this time, the model estimating unit detects the observation voltage change amount $\Delta v$ as a result of the saccadic movement (amount of change in the voltage observed at the electrode when the user is gazing at the reference index 3003 and when the user is gazing at the calibration index 3004, and records calibration data pair ($\theta$, $\Delta v$). The observation voltage change amount $\Delta$ by saccadic movement will be described later.

(2) When the calibration index 3004 disappears, the user gazes at the reference index 3003 again.

(3) (1) and (2) are repeated up to No. 1 to No. 15 of the calibration index 3004 (provided in a matrix of three rows and five columns, at intervals of 25° horizontally, and 15° vertically).

(4) Furthermore, the model estimating unit obtains calibration data at a plurality of positions z (for example, z=20 cm, 50 cm, z=100 cm, . . . ), by moving the position of the monitor 3000 or moving the position of the user 3005, and so on.

This allows obtaining a plurality of data pairs (learning data and calibration data) of ($\theta$, $\Delta v$), including a z-direction (depth direction). In addition, since the calibration data is obtained using (high-speed) saccadic movement, it is possible to prevent drift noise (low frequency noise) from being mixed into the calibration data, thus allowing highly accurate calibration.

<2-2 Model Parameter Estimation>

Next, the model estimating unit performs model parameter estimation based on the obtained calibration data. Specifically, the model estimating unit estimates, in accordance with an electro-oculography model (Expression 9), an electro-oculography theoretical value $$\Delta \hat{v}_{i,j} \qquad \text{[Math 19]}$$

which corresponds to M pieces of calibration data ($\theta_i=\Delta v_{i,j}$) (j=1, . . . , M), each of which corresponds to each electrode i (i=1, . . . , N). The model estimating unit calculates a model parameter such that a sum of squared errors (cost function J) between the calculated electro-oculography theoretical value $$\Delta \hat{v}_{i,j} \qquad \text{[Math 20]}$$

and the measured electro-oculogram $\Delta v_{i,j}$ is smallest.

[Math 21]

$$J = \sum_{i=1}^{N} \sum_{j=1}^{M} (\Delta v_{i,j} - \Delta \hat{v}_{i,j})^2 \qquad \text{(Expression 10)}$$

At this time, the model estimating unit (1) optimizes, of the electro-oculography model (Expression 9), the electrode coordinates ($x_e$, $y_e$, $z_e$) that are a parameter of a nonlinear term (reciprocal term of each of $r_1$, $r_2$, $r_3$, and $r_4$), by performing a search; and (2) calculates an optimum value of a linear parameter (predetermined coefficients) $\alpha_1$, $\alpha_2$, $\alpha_3$, and $\alpha_4$ in accordance with a mathematical expression, using the least square method. The following will describe this in detail.

(1) First, the model estimating unit sets an initial value of the electrode coordinates ($x_e$, $y_e$, $z_e$). In the case of not performing a search for the electrode coordinates, it is necessary to accurately measure the electrode coordinates in advance; whereas, in the case of performing the search, rough visual coordinates are provided as an initial value.

(2) Next, the model estimating unit derives a least squares solution of the predetermined coefficients $\alpha_1$, $\alpha_2$, $\alpha_3$, and $\alpha_4$ at the set electrode coordinates.

First, an electro-oculography theoretical value corresponding to M pieces of calibration data, which is $$\hat{v}_j (j=1{\sim}M) \qquad \text{[Math 22]}$$

is represented in a matrix in accordance with (Expression 11) below.

[Math 23]

$$\begin{pmatrix} \hat{v}_1 \\ M \\ \hat{v}_M \end{pmatrix} = \begin{pmatrix} 1/r_{1,1} & 1/r_{1,2} & 1/r_{1,3} & 1/r_{1,4} \\ M & M & M & M \\ 1/r_{M,1} & 1/r_{M,2} & 1/r_{M,3} & 1/r_{M,4} \end{pmatrix} \begin{pmatrix} \alpha_1 \\ \alpha_2 \\ \alpha_3 \\ \alpha_4 \end{pmatrix} \qquad \text{(Expression 11)}$$

$$\Leftrightarrow \hat{v} = A\alpha$$

Here, $r_{j,1}$, $r_{j,2}$, $r_{j,3}$, and $r_{j,4}$ represent, respectively, the right-eye corneal distance, the right-eye retinal distance, the left-eye corneal distance, and the left-eye retinal distance at the time of measuring a j-th calibration data. Since all the parameters regarding the matrix A including electrode coordinates and the other parameters are set, the matrix A is a constant matrix.

This is prepared for each electrode i (i=1, ..., N). That is, all the electro-oculography theoretical values are represented by (Expression 12) below:
[Math 24]

$$\hat{v}_i = A_i \alpha_i \quad \text{(Expression 12)}$$

Here, a potential of each electrode is a potential for the reference electrode (or ground electrode). Thus, the model estimating unit calculates an electro-oculography theoretical value of a reference electrode R shown in (Expression 13) below in the same manner.
[Math 25]

$$\hat{v}_R = A_R \alpha_R \quad \text{(Expression 13)}$$

With this, the model estimating unit calculates, in accordance with (Expression 14) below, a potential $$\Delta \hat{v}_{i,j} \quad \text{[Math 26]}$$

which is a potential corresponding to the potential generated at each electrode and corresponding to the reference electrode in accordance with:
[Math 27]

$\Delta \hat{v}_{i,j} = v_{i,j} - v_{R,j}$ (Expression 14) so as to calculate $\alpha_i$ (i= 1, ..., N) and $\alpha_R$ such that the cost function J as shown in (Expression 15) below is smallest:

[Math 28]

$$J = \sum_{i=1}^{N} \sum_{j=1}^{M} (\Delta v_{i,j} - (v_{i,j} - v_{R,j}))^2 \quad \text{(Expression 15)}$$

That is, by solving (Expression 16) below to express the solution in a matrix, it is possible to obtain a normal equation as shown in (Expression 17) below:

[Math 29]

$$\frac{\partial J}{\partial \alpha_i} = 0, \quad \frac{\partial J}{\partial \alpha_R} = 0 \quad \text{(Expression 16)}$$

[Math 30]

$$A_i^t (A_i \alpha_i - A_R \alpha_R - \Delta v_i) = 0 \quad \text{(Normal equation)}$$

$$A_R^t \left( \sum_{i=1}^{N} A_i \alpha - N A_R \alpha_R - \sum_{t=1}^{N} \Delta v_i \right) = 0 \quad \text{(Expression 17)}$$

When solving this normal equation, it is possible to obtain (Expression 18) below:

[Math 31]

$$\alpha_R = -\left( A_R^t \left( \sum_{i=1}^{N} B_i \right) A_R \right)^{-1} A_R^t \left( \sum_{i=1}^{N} B_i \Delta v_i \right) \quad \text{(Expression 18)}$$

$$\alpha_i = (A_i^t A_i)^{-1} A_i^t (A_R \alpha_R + \Delta v_i)$$

(However, $B_i = A_i (A_i^t A_i)^{-1} A_i^t - I$,
where $I$ is a unit matrix).

That is, the model estimating unit can obtain the least squares solution of the cost function J (Expression 15), by calculating the predetermined coefficients $\alpha_R$ and $\alpha_i$ in accordance with (Expression 18). Note that other than the method of directly solving the normal equation, the least squares solution of the cost function J (Expression 11) may be calculated using a house holder QR decomposition method and so on.

The model estimating unit searches for the electrode coordinates ($x_e$, $y_e$, $z_e$) using a nonlinear optimization technique (gradient descent method, Levenberg-Marquardt method, and so on), by repeating the processing (1) and (2) described above until the cost function J (Expression 11) falls within a predetermined error range. In addition, the model estimating unit may set an electrode search range and search for all the electrode coordinates based on a predetermined granularity. For example, since a displacement of the electrode often falls within a maximum range of 5 cm or less, the electrode coordinates may be searched for at intervals of 5 mm, based on a search range of ±5 cm in each of the x-, y-, and z-directions with respect to the initial value (visual measurement position of the electrode).

As described above, the model parameter estimating method optimizes a nonlinear parameter (the electrode coordinates) by search, and calculates an optimal value of a linear parameter (the predetermined coefficients) in accordance with mathematical expressions. This allows highly-accurate high-speed estimation of an optimum model parameter. In addition, normally, the electro-oculogram is generated in front and back of the ear, and even in the ear. This method has advantages of allowing, by further considering the electro-oculogram generated at the reference electrode (or ground electrode), highly-accurate estimation and freedom in attachment position of the reference electrode.

Note that attachment of the reference electrode to a position at which no electro-oculogram is generated (earlobe, and so on) simplifies the formula for calculating the least squares solution described above, thus allowing reducing an amount of calculation and circuit size. In addition, by assuming all the predetermined coefficients $\alpha_1$, $\alpha_2$, $\alpha_3$, and $\alpha_4$ as an identical value, it is possible to calculate, despite decrease in model accuracy, the optimum value with high speed by simple calculation.

Figure 5:
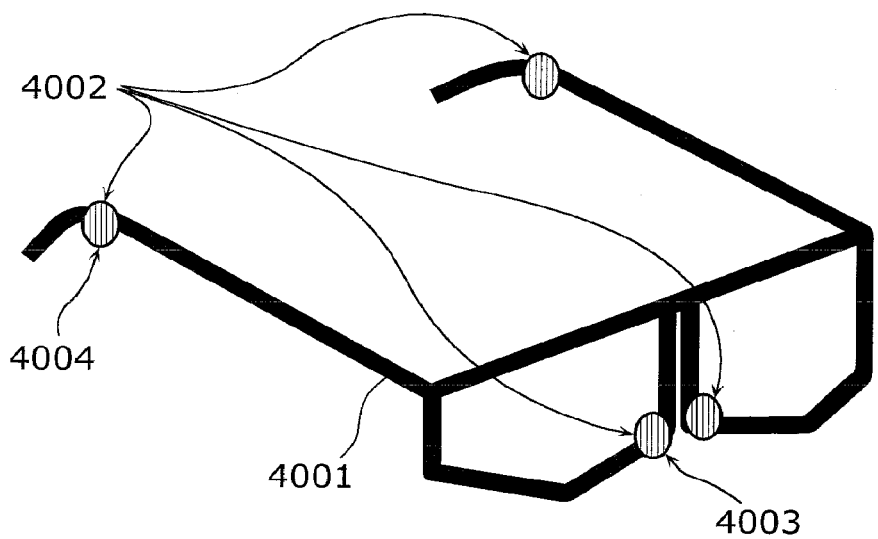
FIG. 5 is a schematic diagram of an example of electrode layout in an eyeglass-type configuration according to the first embodiment of the present invention.
Figure 6:
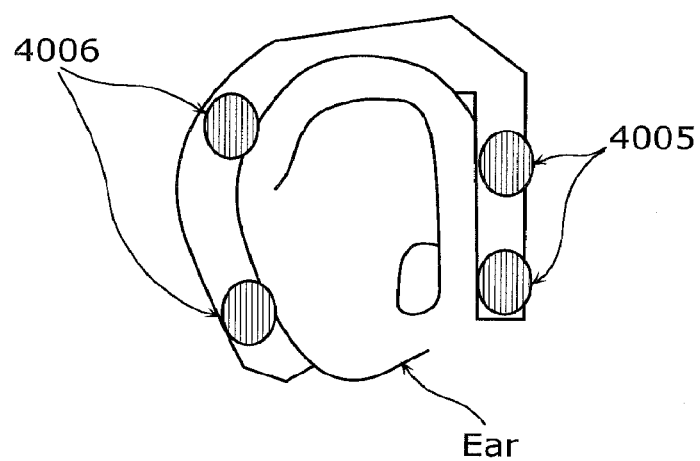
FIG. 6 is a schematic diagram of an example of electrode layout in an on-ear configuration according to the first embodiment of the present invention.

Note that in the case of attaching a plurality of electrodes, the electrodes may be attached in the z-direction with spaces. This allows increasing amplitude in response to the vergence movement, and increases recognition accuracy in the z-direction. As shown in FIG. 5, in the case of incorporating an electrode 4002 into eyeglasses 4001, it is preferable to incorporate the electrode 4002 at a nose-pad position 4003 and a frame-ear contact position 4004. In addition, as shown in FIG. 6, in the case of incorporating the electrode 4002 into an on-ear part, electrodes 4005 and 4006 may be provided in front and rear portions of the ear.

<3 Generating Electro-Oculography Conversion Function>

A model estimating unit calculates an electro-oculography conversion function for the three-dimensional gaze position θ, using a model parameter (electrode coordinates and predetermined coefficients) estimated as described above, in accordance with the following equation:
[Math 32]

$$eog_i(\theta) = \Delta \hat{v}_i = v_i - v_R \quad \text{(Expression 19)}$$

Note that since the electro-oculography conversion function above is a nonlinear function, the function may be held in a look-up table (LUT), thus allowing reducing amount of calculation or circuit scale.

As described above, in the eye-gaze tracking device 1 according to the first embodiment of the present invention, it is possible to calibrate the electro-oculography conversion function with high accuracy, using an electro-oculography model that considers influences of an amount of cross talk between both eyes, and tissues around the eyeball.

<Drift Estimating Method and Eye-Gaze Estimating Method>

Next, the drift estimating method and the eye-gaze tracking method according to the present embodiment will be described with reference to FIGS. 7 to 10.

According to the present embodiment, the drift is estimated using: a difference in spatial distribution characteristics between electro-oculogram and the drift, and an amplitude constraint of the electro-oculogram. Specifically, in a multi-dimensional voltage space observed by a plurality of electrodes, it is possible to determine, as a drift, any component other than an electro-oculography subspace (hereinafter, also referred to as "electro-oculography") mapped by the electro-oculography conversion function for a presence space $\Theta$ in which the gaze position $\theta$ is present (for example, $-50° \leq \theta_x \leq 50°$, $-50° \leq \theta_y \leq 30°$, $z \geq 10$ cm). In other words, it is possible to determine, as a drift component, an electro-oculography component of a portion exceeding the electro-oculogram in the case where the gaze position $\theta$ is present in the presence space $\Theta$ of the gaze position $\theta$. Here, the "electro-oculography subspace" may be calibrated in advance or may be dynamically estimated.

Figure 7:
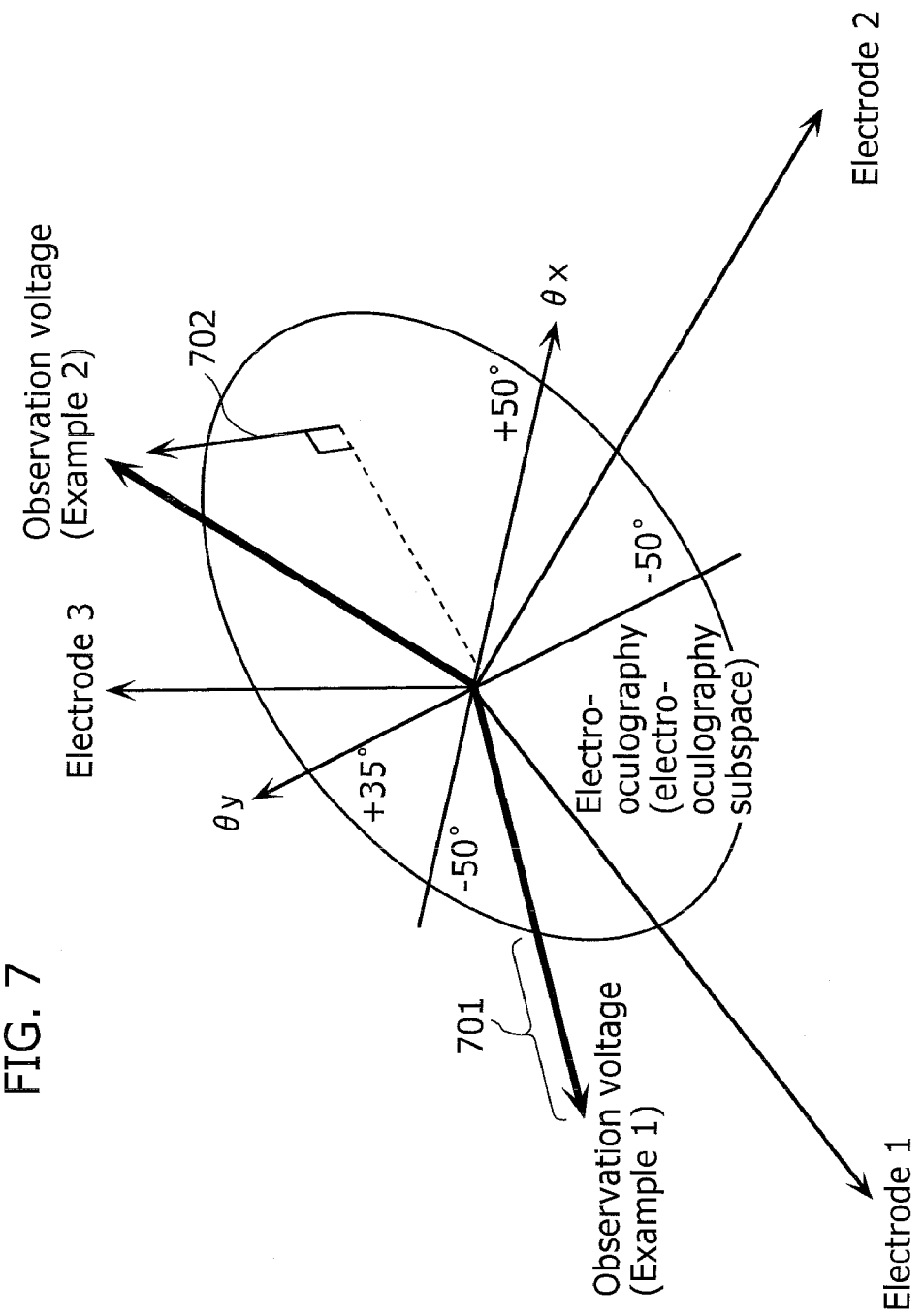
FIG. 7 is a conceptual diagram of a drift correction method according to the first embodiment of the present invention.

FIG. 7 shows a conceptual diagram of a drift correction method when assuming that three electrodes (except for the reference electrode) are provided and that the gaze is two-dimensional including only horizontal and vertical directions. In the three-dimensional voltage space, as a component that is present outside the electro-oculography that is a space in which the electro-oculogram is present, (1) a component 701 that exceeds an electro-oculography range (hundreds of uV) and (2) a component 702 that is orthogonal to the electro-oculography (a component in a normal direction with respect to each point in oculography) are assumed as drift components and removed from the observation voltage. In a word, the drift is removed by continuously removing, from the observation voltage, the residual difference from the electro-oculography.

FIG. 7 represents an electro-oculography space, and the electro-oculography space is an n-dimensional space in the case of n electrodes. Each axis of the electro-oculography space corresponds to a possible voltage value that can be observed by each electrode, and the electro-oculography subspace can be obtained by plotting a possible electro-oculogram for every gaze position $\theta$ within the presence space $\Theta$ in which the gaze point $\theta$ is present. In other words, the electro-oculography subspace is a presence space in which the electro-oculogram or an electro-oculography vector (a vector from the origin to the electro-oculogram) is present.

Figure 8:
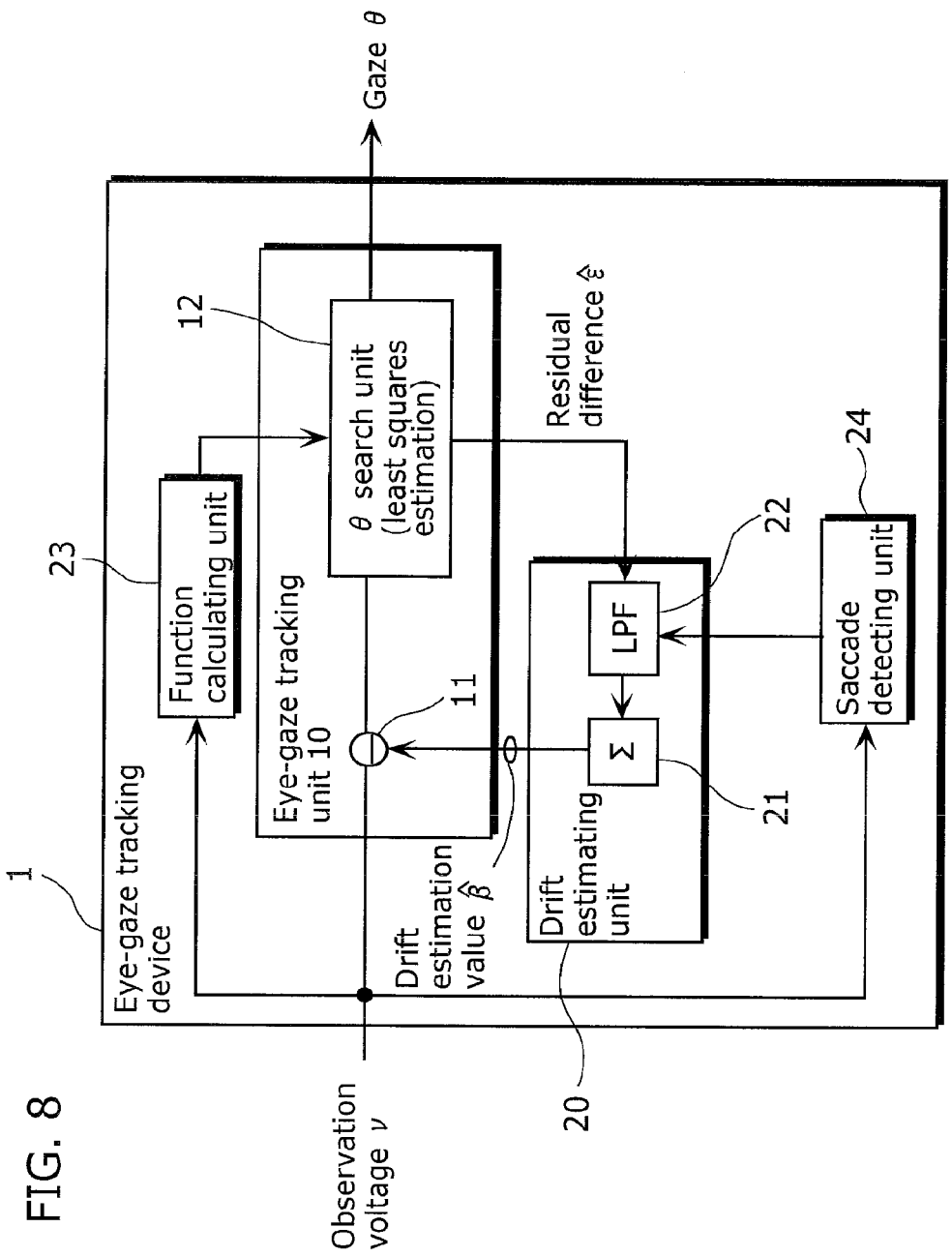
FIG. 8 is a block diagram showing an eye-gaze tracking device 1 according to the first embodiment of the present invention.
Figure 9:
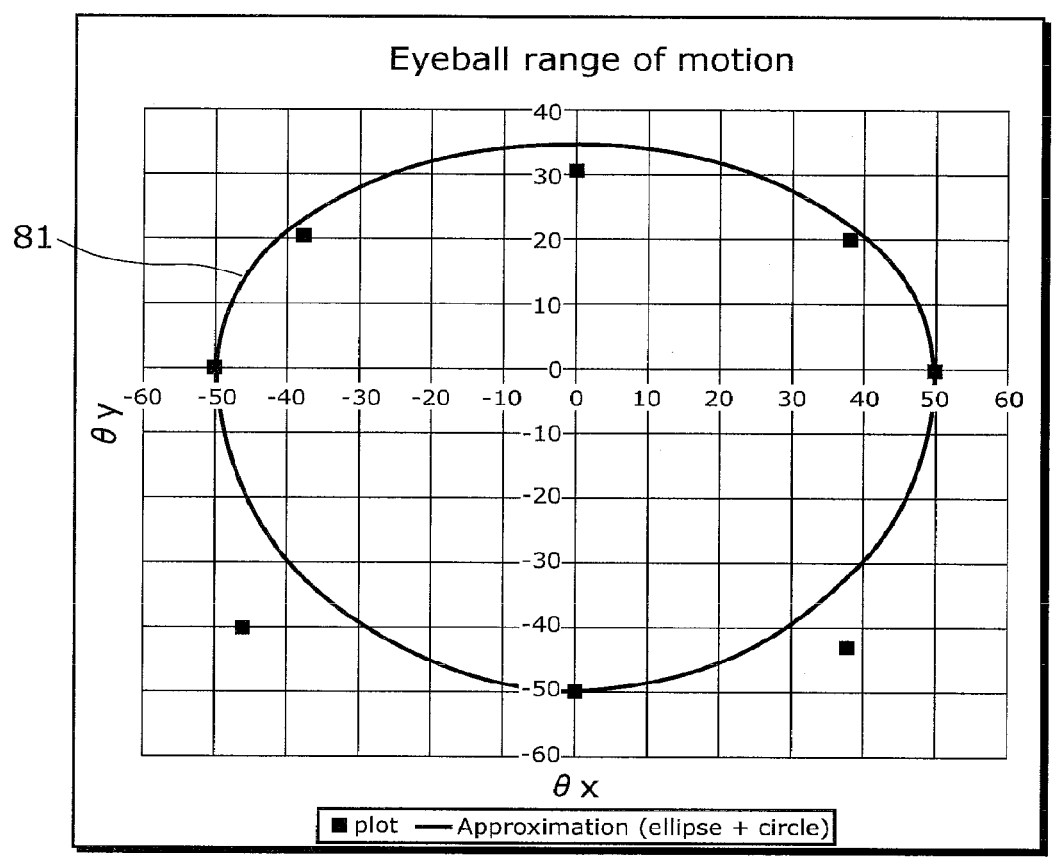
FIG. 9 is a diagram showing an example of an eyeball range of motion according to the first embodiment of the present invention.

The following will describe this in detail with reference to FIGS. 8 and 9.

FIG. 8 is a block diagram showing an eye-gaze tracking device 1 according to the first embodiment of the present invention.

The eye-gaze tracking device 1 includes an eye-gaze tracking unit 10, a drift estimating unit 20, a function calculating unit 23, and a saccade detecting unit 24.

The drift estimating unit 20 estimates drift noise included in a set of observation voltages among observation voltages that are electro-oculograms generated in a living body and observed at the plurality of electrodes, based on a component outside an electro-oculography subspace that is an assembly of sets of electro-oculograms theoretically observed at a plurality of electrodes.

The electro-oculography subspace can be obtained by mapping, in accordance with a predetermined electro-oculography conversion function, the point included in the gaze vector space indicating the gaze direction (gaze point) of the user within the predetermined range.

The eye-gaze tracking unit 10 detects the gaze direction (gaze position) of the user, based on the signal obtained by removing the drift noise estimated by the drift estimating unit 20 from the plurality of observation voltages.

The function calculating unit 23 calculates the electro-oculography conversion function based on the observation voltage observed at each of the plurality of electrodes for each gaze direction.

The saccade detecting unit 24 detects an occurrence of saccadic movement that is rapid eyeball movement.

The eye-gaze tracking unit 10 includes a subtractor 11 and a $\theta$ search unit 12.

The subtractor 11 removes the drift noise by subtracting the drift noise estimated by the drift estimating unit 20 from the observation voltage.

The $\theta$ search unit 12 detects the gaze direction of the user, based on the signal obtained by removing the drift noise from the observation voltage.

The drift estimating unit 20 includes a integrator 21 and a low-pass filter (LPF) 22.

The low-pass filter 22 performs low-pass filtering on the residual difference that is generated when the $\theta$ search unit 12 detects the gaze direction.

The integrator 21 performs integration on the residual difference passed through the low-pass filter 22.

An observation voltage v that is observed from the living body by a plurality of electrodes is input into the eye-gaze tracking device 1. The subtractor 11 subtracts, from the observation voltage v, a drift estimation value $$\hat{\beta}$$ [Math 33]

which is output from the drift estimating unit 20.

The $\theta$ search unit 12 estimates, in accordance with the electro-oculography conversion function calculated by the function calculating unit 23 or the look-up table prepared based on the electro-oculography conversion function, a gaze estimation value $$\hat{\theta}(t)$$ [Math 34]

which satisfies (Expression 5).

At this time, the $\theta$ search unit 12 outputs $$\hat{\epsilon}$$ [Math 35]

which is a residual difference between the observation voltage and the theoretical voltage corresponding to the gaze estimation value. The low-pass filter 22 performs low-pass filtering on the residual difference. The integrator 21 performs integration on the residual difference passed through the low-pass filter 22. The eye-gaze tracking unit 10 outputs, as the drift estimation value, the value passed through the low-pass filter 22 to the eye-gaze tracking unit 10. The subtractor 11 in the eye-gaze tracking unit 10 subtracts the drift estimation value from the observation voltage v. The low-pass filtering is performed for the purpose of removing a high-frequency noise other than the drift noise included in the residual difference, and thereby estimating the drift noise with higher accuracy. In other words, it is possible to remove the normal distribution noise n(t) in (Expression 4) to leave only drift $\beta(t)$.

The following will describe this operation.

<Basic Operation>

The $\theta$ search unit 12 searches for $$\hat{\theta}(0)$$ [Math 36]

which is a gaze position such that a sum of square errors between the input observed voltage $V_i(0)$ and a theoretical voltage $eog(\theta(0))$ is smallest at time $t=0$.

[Math 37]

$$\hat{\theta}(0) = \underset{\theta \in \Theta}{\mathrm{argmin}} \sum_{i=1}^{N} (v_i(0) - eog_i(\theta(0)))^2 \quad \text{(Expression 20)}$$

Here, when searching for a gaze $$\hat{\theta}(t), \quad \text{[Math 38]}$$

the presence space $\Theta$ of the gaze position $\theta$ is defined, for example, as: $-50° \leq \theta_x \leq 50°$, $-50° \leq \theta_y \leq 30°$, $z \geq 10$ cm. In addition, as shown in FIG. 9, a gaze presence space (eyeball limit of motion) 81 is limited to an ellipse which is vertically asymmetrical. This is based on the fact that upward motion of the human eye is smaller than downward motion. Specifically, in the region $\theta_y \geq 0$, the gaze presence space 81 is assumed as: approximately, the long axis $\theta_x=50°$, and the short axis $\theta_y=35°$. In addition, in the region $\theta_y<0$, the gaze presence space 81 is assumed as a circle of 50° in radius. Thus, it is possible to increase accuracy in separating the drift noise from the electro-oculography, by restricting the upper range.

In addition, at this time, it is preferable to previously hold, in the three-dimensional look-up table, the theoretical voltage $eog(\theta(t))$ at each gaze position $\theta=(\theta_x, \theta_y, z)$, because this reduces circuit scale or the amount of calculation. Note that, in consideration of the case where gazes of both eyes do not cross each other at a point, the gaze position may be four-dimensionally represented as $(\theta_{rx}, \theta_{ry}, \theta_{lx}, \theta_{ly})$ and may be held in a four-dimensional look-up table.

Note that the method of detecting the gaze position is not limited to the method of minimizing the least square error, but any method that minimizes the error between the observation value and the theoretical value may be used, such as methods using another evaluation function (high-order statistics, entropy, and so on), and techniques such as the Kalman filter or the Monte Carlo filter.

At this time, the drift estimating unit 20 records a residual difference
[Math 39]

$$\hat{\epsilon}(0) = v(0) - eog(\hat{\theta}(0)) \quad \text{(Expression 21)}$$

Note that since the search range $\Theta$ in the gaze position $\theta$ is limited, a residual vector $$\hat{\epsilon}(t) \quad \text{[Math 40]}$$

includes not only a component orthogonal to the electro-oculography but also a component outside the electro-oculography range. More specifically, not only (2) the component orthogonal to electro-oculography, but also (1) the component that exceeds electro-oculography range (hundreds of uV) is included as shown in FIG. 7.

After this, first, the drift estimating unit 20 calculates, at time t, a drift prediction value $$\hat{\beta}(t) \quad \text{[Math 41]}$$

in accordance with:
[Math 42]

$$\hat{\beta}(t) = \hat{\beta}(t-\Delta t) + \hat{\epsilon}(t-\Delta t) \quad \text{(Expression 23)}$$

Here, it is assumed that $$\hat{\beta}(0) = 0. \quad \text{[Math 43]}$$

In addition, $\Delta t$ represents A/D sampling time, or sampling time that is down-sampled.

Next, the $\theta$ search unit 12 searches for a gaze such that a sum of the square errors between the observation voltage vi(t) and the theoretical voltage $$eog(\theta(t)) + \hat{\beta}(t) \quad \text{[Math 44]}$$

which is calculated using the electro-oculography conversion function and the drift prediction value is smallest, so as to search out $$\hat{\theta}(t) \quad \text{[Math 45]}$$

which is the gaze (search range $\Theta$).

[Math 46]

$$\hat{\theta}(t) = \underset{\theta \in \Theta}{\mathrm{argmin}} \sum_{i=1}^{N} \left( v_i(t) - \left( eog_i(\theta(t)) + \hat{\beta}_i(t) \right) \right)^2 \quad \text{(Expression 23)}$$

At this time, the drift estimating unit 20 records
[Math 47]

$$\hat{\epsilon}(t) = \theta(t) - eog(\theta(t)) + \hat{\beta}(t)) \quad \text{(Expression 24)}$$

which is the residual difference.

As described above, the drift is removed by continuously removing a voltage component outside the electro-oculography by feed back, and suppressing the observation voltage within the electro-oculography.

<Modification>

In the basic configuration described above, in some cases, the residual difference includes a high-frequency noise, which causes a correction error when fed back to the observation voltage. Thus, it is preferable to remove the high-frequency noise from the residual error using the low-pass filter. This processing is performed by the low-pass filter 22.
[Math 48]

$$\hat{\beta}(t) = \hat{\beta}(t-\Delta t) + LPF(\hat{\epsilon}(t-\Delta t)) \quad \text{(Expression 25)}$$

Here, LPF( ) represents the low-pass filter.

At this time, since a faster correction response to the drift component is preferable, it is preferable to use a filter having a short filter length. For example, a two-tap Infinite Impulse Response (IIR) filter may be used as shown below. Note that fc is a cutoff frequency.

[Math 49]

$$\hat{\beta}(t) = \hat{\beta}(t - \Delta t) + \gamma \cdot \hat{\epsilon}(t - \Delta t) \quad \text{(Expression 26)}$$

where $$\gamma = 1 - \frac{1}{1 + 2\pi f_c \Delta t}$$

However, when simply using the low-pass filter, low-pass filtering is performed not only when high-frequency noise occurs but also when high-frequency eyeball movement (saccadic movement or saccadic eye movement) occurs, thus causing deterioration in drift correction responsiveness. Thus, when the saccade detecting unit 24 detects saccadic movement, the low-pass filter 22 may be adaptively weakened. In other words, the cutoff frequency of the low-pass filter 22 may be lowered. Note that the method of detecting saccadic movement will be described later.

In addition, when the gaze estimation value calculated by the $\theta$ search unit 12 exceeds the boundary of the gaze presence space 81 (when the gaze estimation value is present outside the gaze presence space 81), the cutoff frequency of the low-pass filter 22 may be raised. In other words, the cutoff frequency may be changed depending on whether or not the gaze estimation value exceeds the electro-oculography range. For example, when the observation voltage is below the electro-oculography range, the cutoff frequency may be fc=1 Hz in consideration of a calibration error of the electro-oculography, and when the observation voltage is equal to or above the electro-oculography range, the cutoff frequency may be fc=5 Hz to increase correction speed.

In addition, prior to the low-pass filtering, a residual difference having a small amplitude may be ignored in consideration of the calibration error of the electro-oculography (what is known as coring processing).

Figure 10:
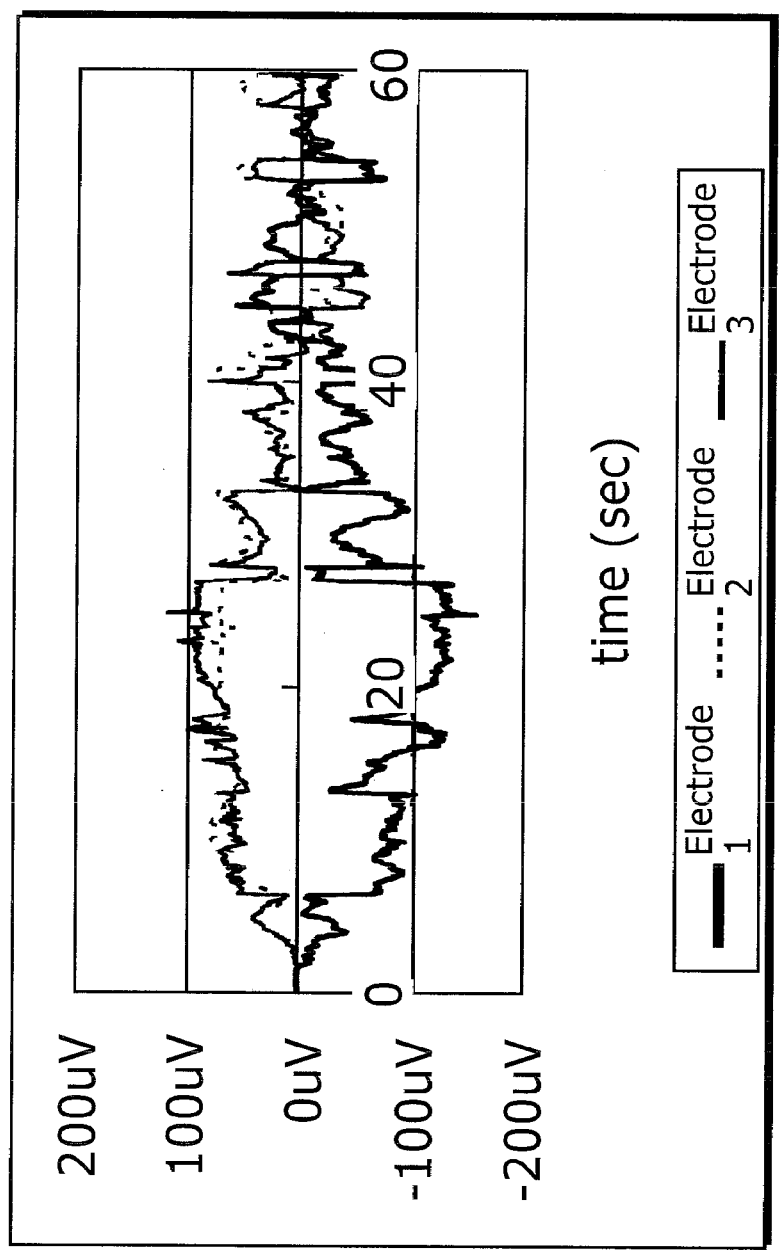
FIG. 10 is an example of a waveform after drift correction according to the first embodiment of the present invention.

As described above, the eye-gaze tracking device 1 according to the first embodiment of the present invention allows suppressing a high-amplitude drift noise to a significant level (to 1/100 or below), as seen in the example of a waveform of the corrected observation voltage (example of the case of providing three electrodes) shown in FIG. 10, by removing the voltage component outside the electro-oculography (drift component) from the observation voltage observed at each electrode position. This allows the eye-gaze tracking device 1 to detect the gaze with high accuracy.

Note that it is possible to calculate each parameter as shown in FIG. 3 from the three-dimensional gaze vector $\theta=(\theta_x, \theta_y, z)$ in accordance with the following expression:

$$\tan\theta_{lx} = \tan\theta_x + \frac{b}{z}, \quad \tan\theta_{rx} = \tan\theta_x - \frac{b}{z}, \quad \text{[Math 50]}$$

$$\tan\theta_{ly} = \tan\theta_y\left(\frac{\cos\theta_{lx}}{\cos\theta_x}\right), \quad \tan\theta_{ry} = \tan\theta_y\left(\frac{\cos\theta_{rx}}{\cos\theta_x}\right)$$

$$z = \frac{2b}{\tan\theta_{lx} - \tan\theta_{rx}} = y\left(\frac{\cos\theta_{lx}}{\tan\theta_y}\right)$$

$$= y\left(\frac{\cos\theta_x}{\tan\theta_y}\right) = y\left(\frac{\cos\theta_{rx}}{\tan\theta_{ry}}\right),$$

$$x = z\tan\theta_x, \quad y = z\left(\frac{\tan\theta_y}{\cos\theta_x}\right)$$

$$L = \frac{z}{\cos\theta_x\cos\theta_y}, \quad L_l = \frac{z}{\cos\theta_{lx}\cos\theta_{ly}},$$

$$L_r = \frac{z}{\cos\theta_{rx}\cos\theta_{ry}}$$

$$\theta_{lx} = \theta_x + \frac{\mu_x}{2}, \quad \theta_{rx} = \theta_x - \frac{\mu_x}{2},$$

$$\cos\mu = \frac{L_l^2 + L_r^2 - 4b^2}{2L_lL_r}$$

By using this relationship to detect, for example, a gaze point distance L, it is possible to apply the eye-gaze tracking method to an application which executes processing in accordance with the distance.

Note that when measuring the electro-oculogram for model parameter estimation, the eyeballs may be circularly rotated two times. In other words, the potential at the boundary of the electro-oculography subspace corresponds to the potential at the boundary of the gaze presence space. For this reason, it is possible to prepare the electro-oculography subspace, based on the electro-oculogram obtained when the user circularly rotates the eyeballs by 360 degrees up to the limit. In addition, by recording a first observation voltage and a second observation voltage that are observed at the same point and interpolating a voltage between these points, to thereby estimate the drift occurring during measurement of the two observation voltages, and removing the drift from one of the observation voltages, it is possible to measure the electro-oculogram with high accuracy without being affected by the drift. Note that being "circular" need not be a precise circle but is a curve different from user to user. In addition, the same point need not be completely "the same" but may be more or less different.

In addition, the nonlinear electro-oculography conversion function may be prepared not by the electro-oculography model. In other words, the voltage of a gaze position at which no voltage has been obtained may be calculated by performing interpolation using the gaze position and observation voltage included in the calibration data that is measured. This allows reducing circuit scale or the amount of calculation for preparing the electro-oculography conversion function.

Note that, although depending on where to attach the electrodes, in the linear model, a larger gaze angle results in a larger error of the electro-oculography conversion function (approximately 5° to 10°), thus deteriorating drift estimation accuracy (drift noise estimation accuracy) and gaze direction estimation accuracy. Particularly, in the feedback configuration as shown in FIG. 8, a linear approximation error is accumulated as the drift estimation error. However, due to the highly-accurate electro-oculography conversion function that considers nonlinearity of electro-oculograms, use of the nonlinear model allows highly accurate electro-oculography measurement and gaze detection.

The saccade signal detecting method mentioned earlier will be described. Note that hereinafter, the observation voltage is also referred to as an electro-oculography original signal.

Figure 11:
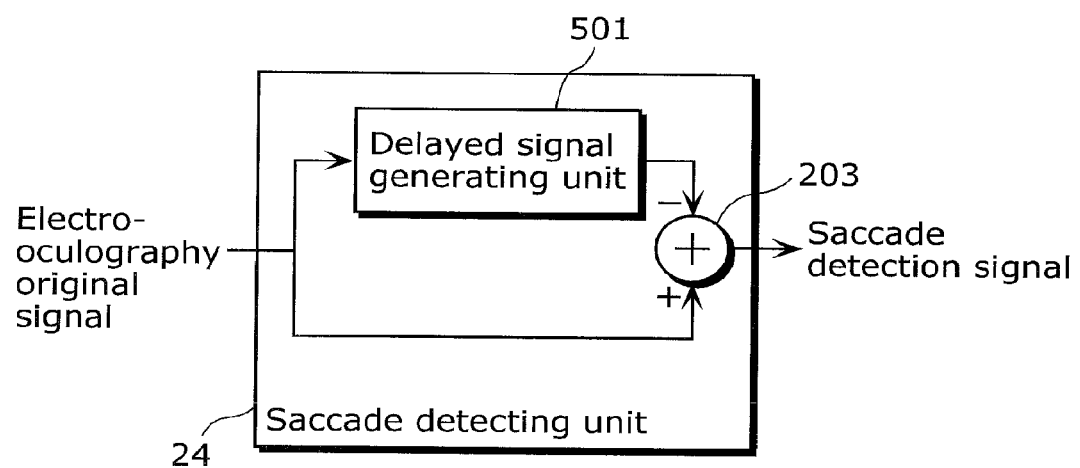
FIG. 11 is a block diagram of a saccade detecting unit according to the first embodiment of the present invention.
Figure 12:
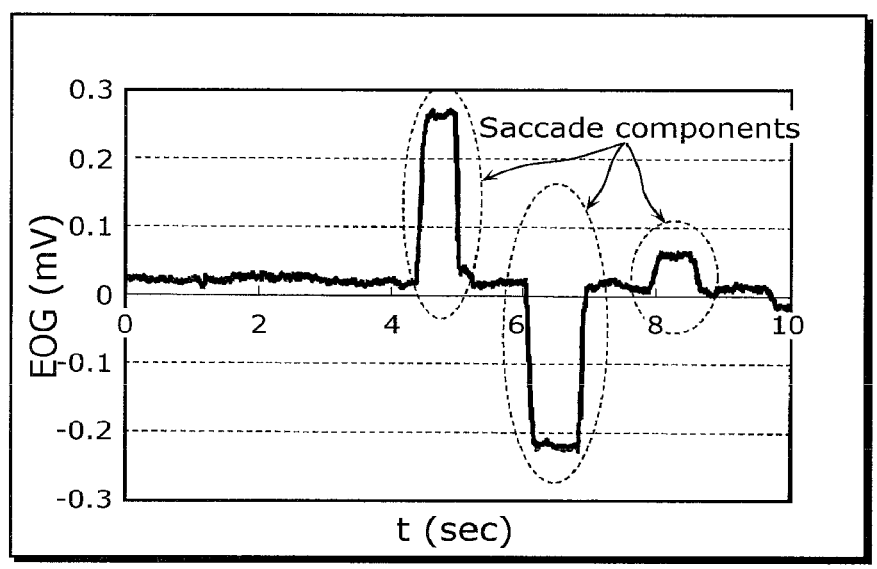
FIG. 12 is a diagram showing an example of an electro-oculography signal including a saccade signal.

FIG. 11 shows a block diagram of the saccade detecting unit 24.

The saccade detecting unit 24 includes a delayed signal generating unit 501 and a subtraction unit 203. The delayed signal generating unit 501 delays the electro-oculography original signal for a predetermined delay time and outputs a delayed signal. In addition, the electro-oculogram original signal input into the saccade detecting unit 24 is branched into two signals. Then, one of the branched signals is input into the subtraction unit 203 as the delayed signal via the delayed signal generating unit 501 and the other is directly input into the subtraction unit 203. Then, the subtraction unit 203 subtracts the delayed signal from the electro-oculography original signal, to output a saccade signal. It is possible to easily obtain a plus and minus signed saccade signal by including the delayed signal generating unit 501.

Processing performed by the delayed signal generating unit 501 as shown in FIG. 11 will be described. The delayed signal generating unit 501 performs the following processing on an electro-oculography original signal f(x):

$$f\text{delay}(x)=f(x-t)$$

Figure 13:
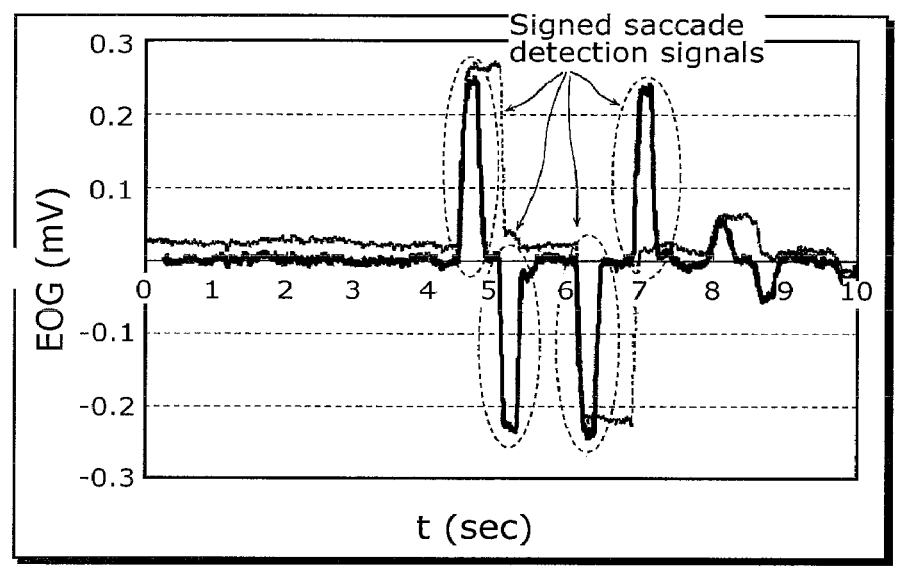
FIG. 13 is a diagram showing a saccade detection signal when a delay time for a delayed signal generating unit is 0.25 minutes.

Here, fdelay (x) is an electro-oculography signal after delay processing, and t is a delay time. The delayed signal can be obtained by performing the delay processing described above on the electro-oculography original signal shown in FIG. 12. Then, FIG. 13 shows an example where the subtraction unit 203 subtracts the delayed signal from the electro-oculography original signal. Note that, to detect a signed saccade component, the delay time is set to t=0.25 seconds. FIG. 13 shows that the signed saccade signal including the period of time during which the saccade occurred is obtained.

The saccade detecting unit 24 generates a saccade detection signal and an electro-oculography change amount based on an output signal from the subtraction unit 203 as shown in FIG. 13, to output the generated saccade detection signal and the electro-oculography change amount to the low-pass filter 22. For example, when the amount of change in sampled values within a period of time corresponding to a period of time required for a saccadic movement exceeds a predetermined threshold, it is determined that a saccadic movement has occurred, so that a saccade detection signal is output. In addition, the amount of change in sampled values at this time is output as an electro-oculography change amount.

Figure 14:
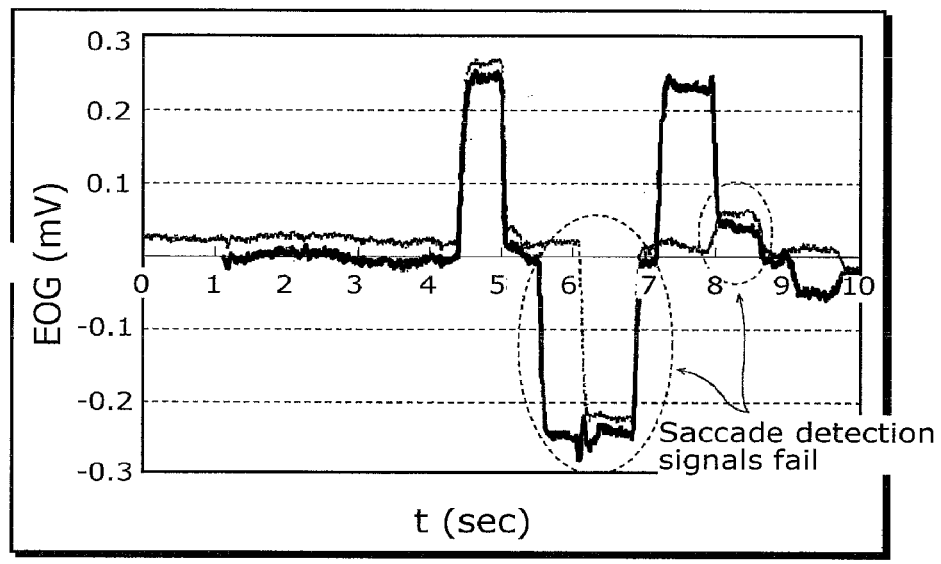
FIG. 14 is a diagram showing a saccade detection signal when a delay time for a delayed signal generating unit is 1.1 seconds.

Here, when the delay time t becomes larger than a general single fixation time=(approximately 0.3 to 0.4 seconds), the saccade signal fails as shown in FIG. 14. FIG. 14 is an example where the delay time t is 1.1 seconds. When the saccade signal fails as shown in FIG. 14, the saccade signal cannot be extracted. Thus, it is necessary to make the delay time t of the delayed signal generating unit 501 shorter than the general single fixation time. Note that, although the second embodiment has shown an example where the delay time of 0.25 seconds is applied, any value may be applied as long as the delay time is shorter than the general single fixation time.

According to the configuration as described above, the configuration is effective in making it possible to distinguish between a plus and a minus signal by generating a delayed signal from an electro-oculography original signal to thereby detect a signed saccade signal.

<Method of Removing Blink Signal>

Next, a saccade tracking method in consideration of an effect of a blink will be described.

Figure 15:
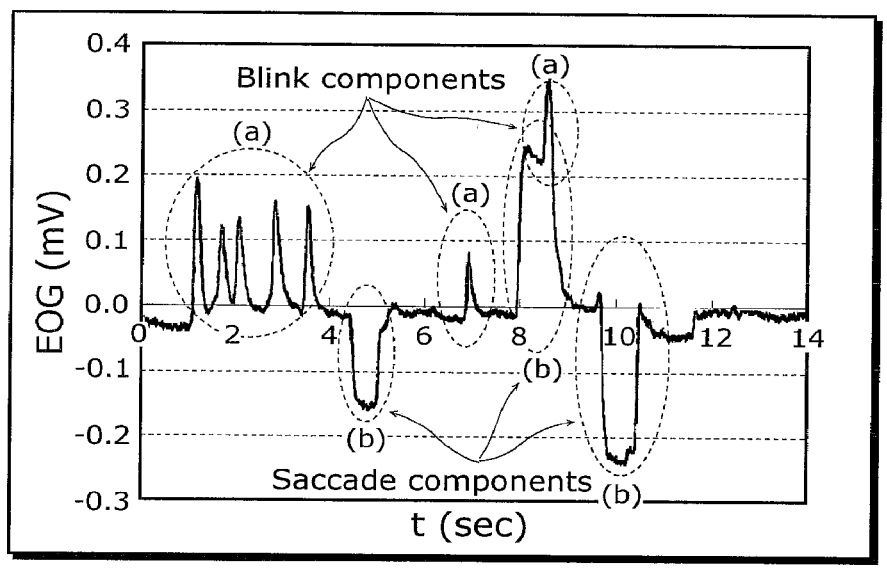
FIG. 15 is a diagram showing an example of an electro-oculography signal including a blink signal.

When the user blinks, as shown in a region (a) in FIG. 15, there is a case where a rapid potential (that is a "blink signal") is generated in a plus direction. For this reason, only with the method described above, it is not possible to detect only the saccade signal, thus causing degradation in calibration accuracy in some cases.

Figure 16:
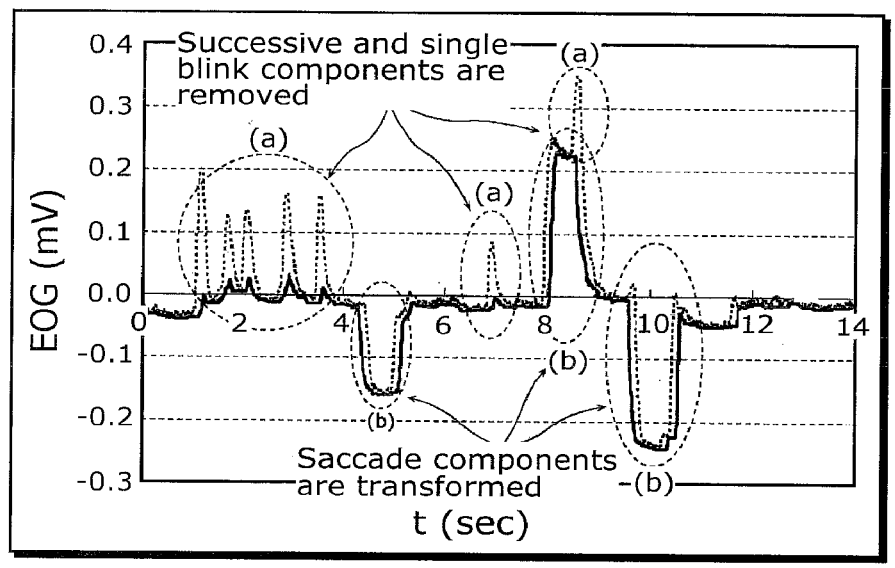
FIG. 16 is a diagram showing an electro-oculography signal obtained by applying minimum value filtering to the electro-oculography signal in FIG. 15.
Figure 17:
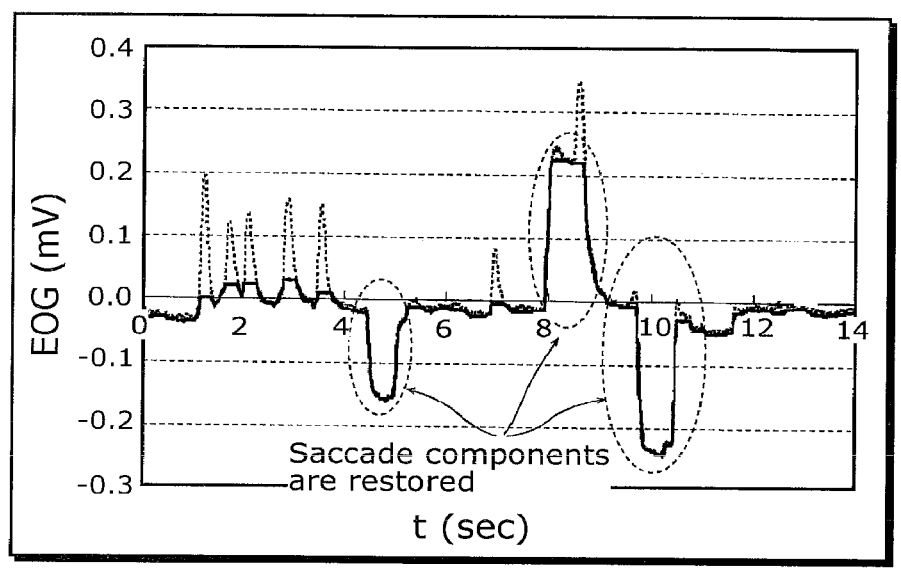
FIG. 17 is a diagram showing an electro-oculography signal obtained by applying maximum value filtering to the electro-oculography signal in FIG. 15.

Thus, the blink signal is removed by applying the minimum value filter as shown in FIG. 16. However, only with this, a portion indicating change in voltage (saccade component) by saccadic movement is transformed. Thus, by further applying the maximum value filter, the saccade component is restored as shown in FIG. 17.

Note that there is a case where the sign of the blink signal becomes minus depending on the attachment position of the electrode. When the blink signal is minus, the maximum value filter and the minimum value filter may be reversed in application order.

In addition, a filter length of the minimum value filter and the maximum value filter may be set to a value that is larger than a length of time for a general single blink (approximately 0.15 seconds to 0.2 seconds), and is smaller than a length of a single fixation time (approximately 0.3 seconds to 0.4 seconds).

In addition, in the case where only removing a blink signal is intended, only one of the minimum value filter and maximum value filter may be applied.

As described above, the signal from which the blink signal is removed is input into the saccade detecting unit 24 shown in FIG. 11, as the electro-oculography original signal. This allows highly-accurate calibration without being affected by blinking. This removal of the blink signal is performed by a blink signal removing unit provided outside the eye-gaze tracking device 1 and is not shown in the figure.

(Second Embodiment)

Next, an eye-gaze tracking device according to a second embodiment will be described.

The eye-gaze tracking device according to the second embodiment has the same configuration as the eye-gaze tracking device 1 according to the first embodiment as shown in FIG. 8. However, the configuration of the saccade detecting unit is different. The following will describe the saccade detecting unit according to the second embodiment.

Figure 18:
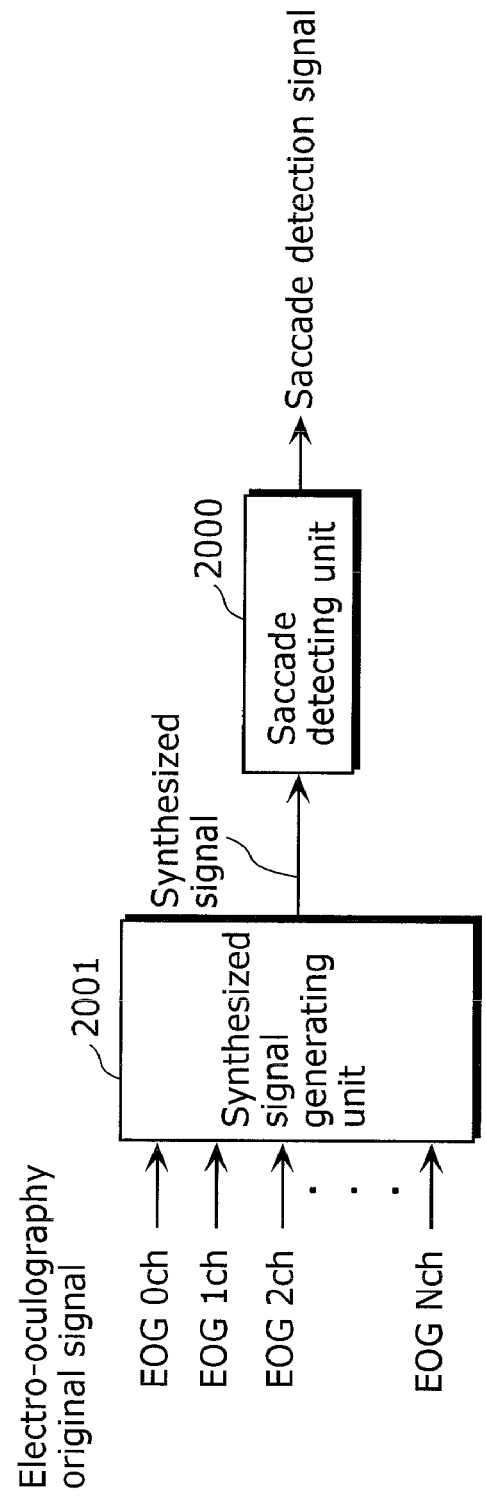
FIG. 18 is a block diagram of a saccade detecting unit according to a second embodiment of the present invention.

FIG. 18 shows a block diagram showing the saccade detecting device according to the second embodiment. This saccade detecting device performs saccade detection processing when measuring the electro-oculography original signal through multiple channels. The saccade detecting device is used in place of the saccade detecting unit 24 in the eye-gaze tracking device 1 according to the first embodiment as shown in FIG. 8.

The saccade detecting device according to the second embodiment includes a synthesized signal generating unit 2001 which generates a synthesized signal from the electro-oculography original signal through multiple channels, and a saccade detecting unit 2000.

Figure 19:
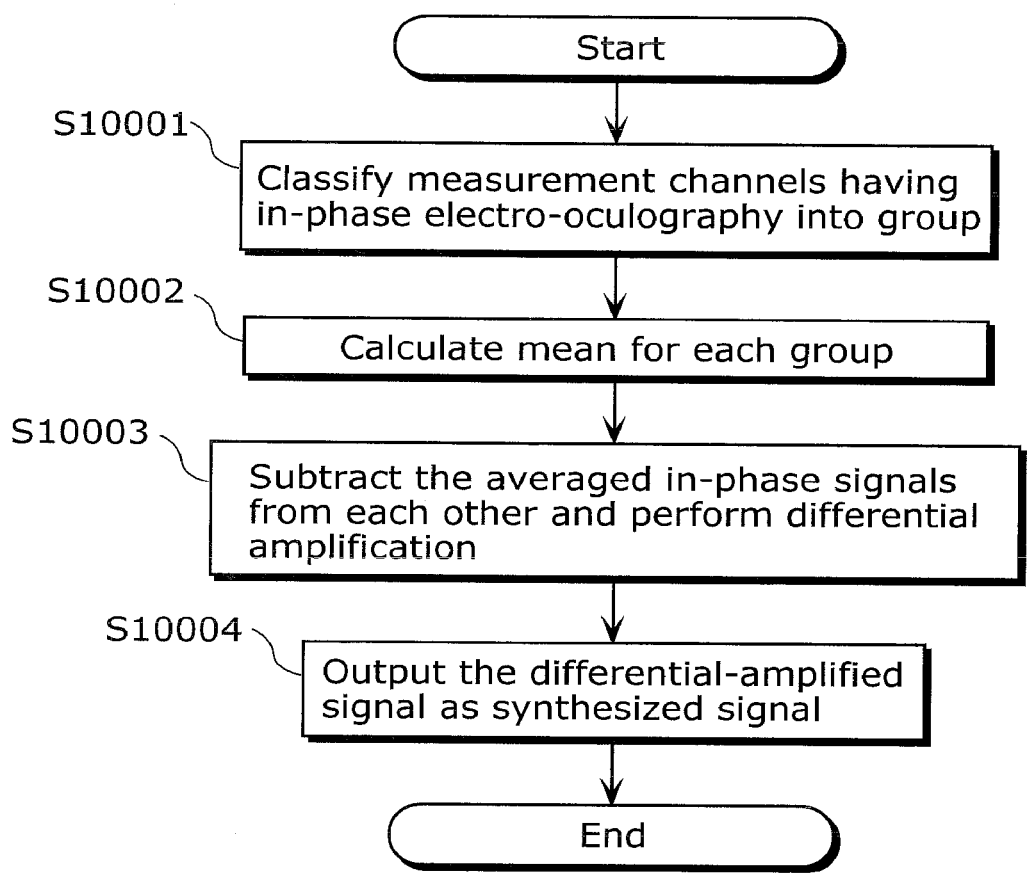
FIG. 19 is a flowchart showing an operation of a synthesized signal generating unit according to the second embodiment of the present invention.

For example, it is possible to consider that the synthesized signal generating unit 2001 generates a synthesized signal by performing averaging using, from among electro-oculography original signals EOG0$ch$ to EOGN$ch$ that have been input, electro-oculograms of measurement channels through which the electro-oculograms are measured in phase with respect to the eyeball movement, and performing differential amplification after subtracting the averaged in-phase signals from each other. FIG. 19 shows a specific processing procedure.

First, grouping of measurement channels having in-phase electro-oculograms is performed (S10001). Here, whether the electro-oculograms are in phase or not can be judged according to the measurement position such as the right side and left side of the face. Note that the judgment may be performed not only by the measurement position but also be dynamically performed based on a feature of the measured electro-oculography signal. Next, averaging is performed on each group resulting from the grouping (S10002). Then, differential amplification is performed by subtracting in-phase signals from each other in each of the averaged groups (S10003), and the signals thus produced are output as a synthesized signal (S10004).

The saccade detecting unit 2000 generates a saccade detection signal, using the synthesized signal generated by the synthesized signal generating unit 2001. The process of generating the saccadic detection signal is performed in the same manner as the process performed by the saccade detecting unit 24 in the first embodiment.

The saccade detecting unit 2000 generates a saccade detection signal and amplitude information, and outputs the generated saccade detection signal and amplitude information to the low-pass filter 22 shown in FIG. 8. For example, when an amount of change in sampled value within a period of time corresponding to an amount of time required for saccadic movement is above a predetermined threshold, it is judged that the saccadic movement has occurred, so that the saccade detection signal is output. In addition, the change amount of the sampled value at this time is output as amplitude information (electro-oculography change amount).

With the configuration according to the second embodiment described above, since a synthesized signal having a high S/N ratio is generated from electro-oculography original signals through multiple channels, and a saccade signal is detected using the synthesized signal; thus, the configuration according to the second embodiment is effective in increasing accuracy in saccade detection.

(Third Embodiment)

Figure 20:
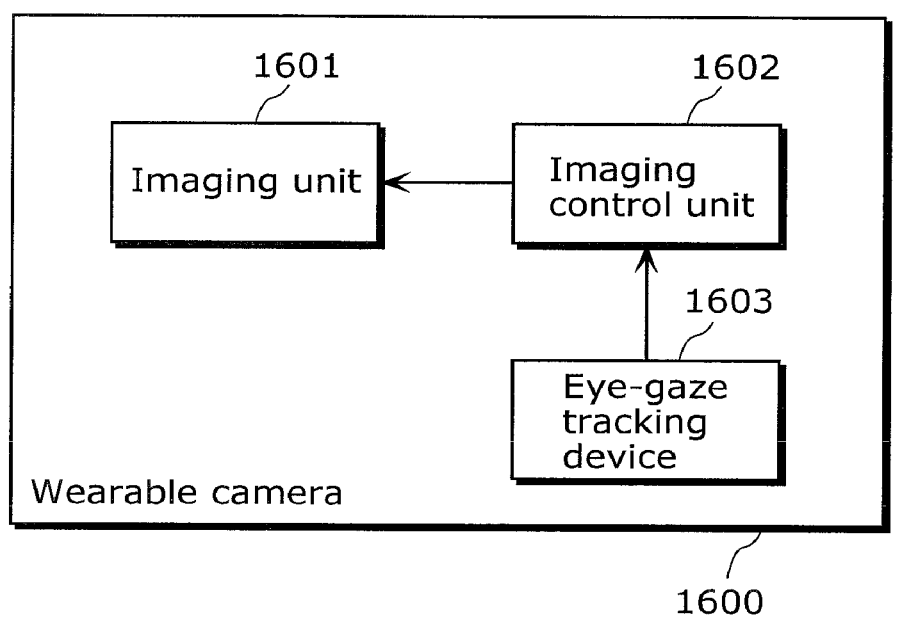
FIG. 20 is a block diagram of a wearable camera according to a third embodiment of the present invention.
Figure 21:
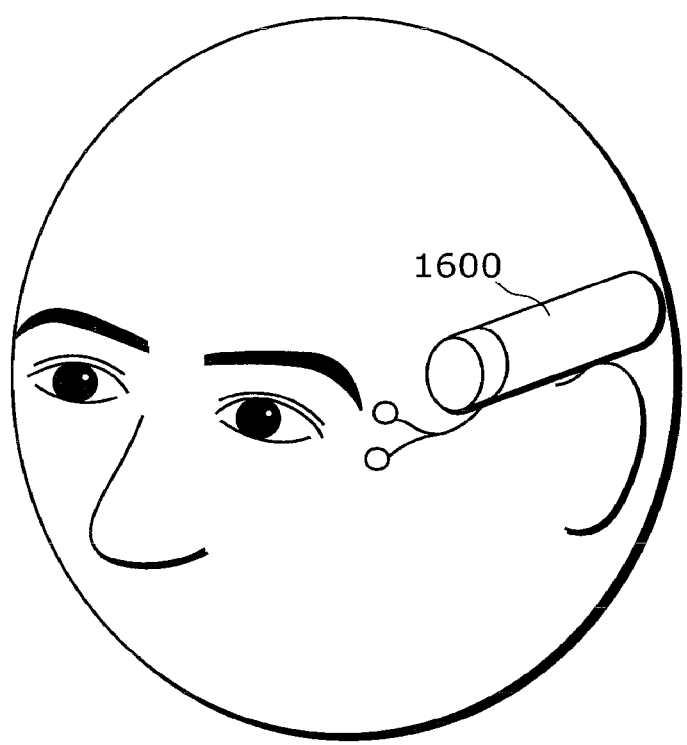
FIG. 21 is a diagram showing a state in which the user is wearing the wearable camera according to the third embodiment of the present invention.

Next, a wearable camera 1600 according to a third embodiment of the present invention will be described with reference to FIGS. 20 and 21. The wearable camera 1600, for example, is attached to a side of the user's head and captures an image in a gaze direction of the user. Specifically, the wearable camera 1600 includes: an imaging unit 1601, an imaging control unit 1602, and an eye-gaze tracking device 1603.

The wearable camera 1600 may be, for example, a camera which captures a still image or a video camera which captures video. To the eye-gaze tracking device 1603, for example, it is possible to apply the eye-gaze tracking device 1 according to the first or second embodiment. In addition, the electrode as an electro-oculography measuring unit in the third embodiment is attached to the user, as shown in FIG. 21, on upper and lower sides of the temple beside the left eye.

Then, the imaging control unit 1602 monitors an output signal from the eye-gaze tracking device 1603, and changes an orientation of the imaging unit 1601 following the movement of the user's gaze. This allows the imaging unit 1601 to capture the gaze direction of the user.

However, the wearable camera 1600 according to the third embodiment is not limited to the use as described above. For other uses, it is also possible to apply the wearable camera 1600 to devices such as a device which plots the user's gaze position detected by the eye-gaze tracking device 1603 on the image captured by the imaging unit 1061, or a device which detects the gaze of a driver to alert danger while driving, or the like.

(Fourth Embodiment)

Figure 22:
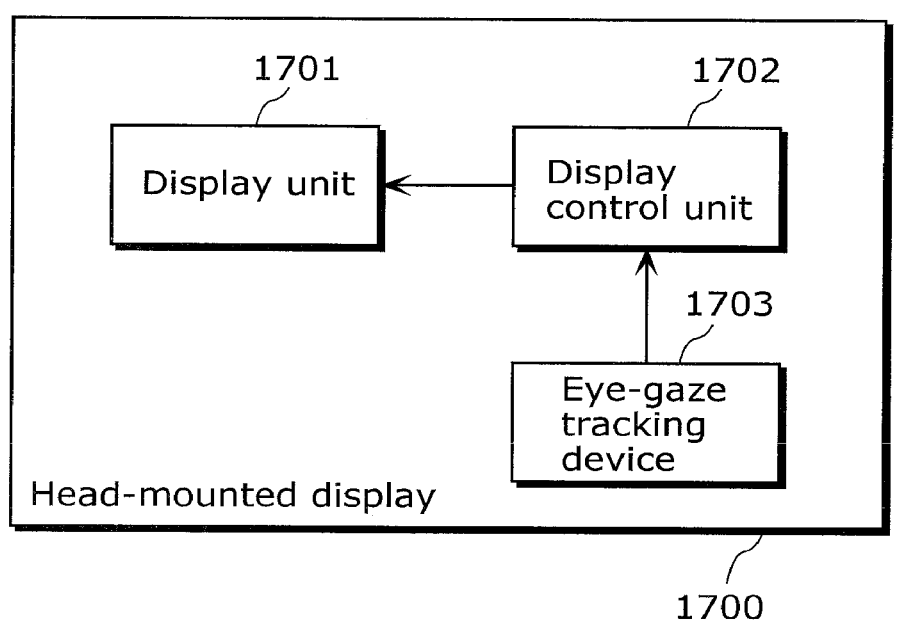
FIG. 22 is a block diagram of a head-mounted display according to a fourth embodiment of the present invention.
Figure 23:
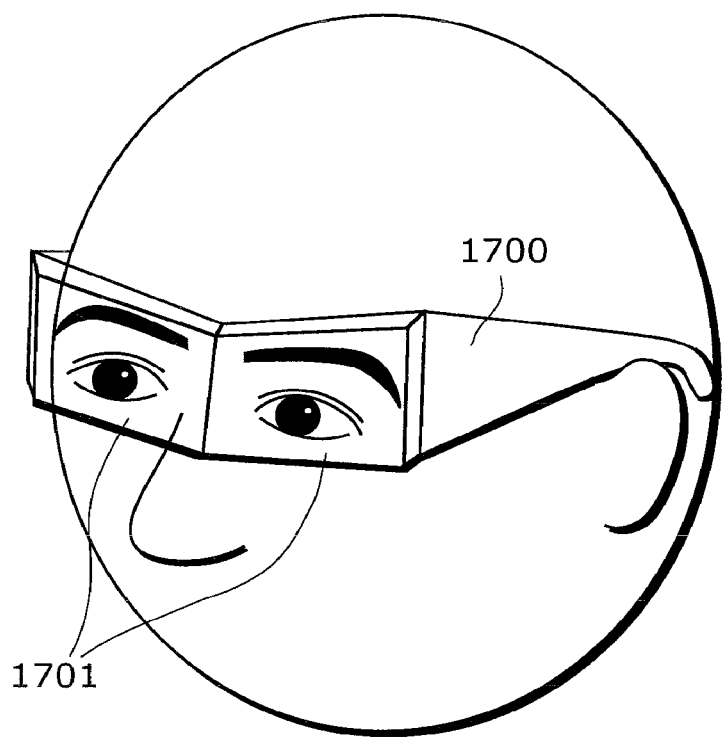
FIG. 23 is a diagram showing a state in which a user is wearing the head-mounted display according to the fourth embodiment of the present invention.

Next, a head-mounted display 1700 according to a fourth embodiment of the present invention will be described with reference to FIGS. 22 and 23. The head-mounted display 1700, for example, has an eyeglass shape, and is a device which displays an image in front of the user's eyes, and moves a mouse pointer that is shown on the displayed image into the user's gaze direction. Specifically, the head-mounted display 1700 includes a display unit 1701, a display control unit 1702, and an eye-gaze tracking device 1703.

Figure 24:
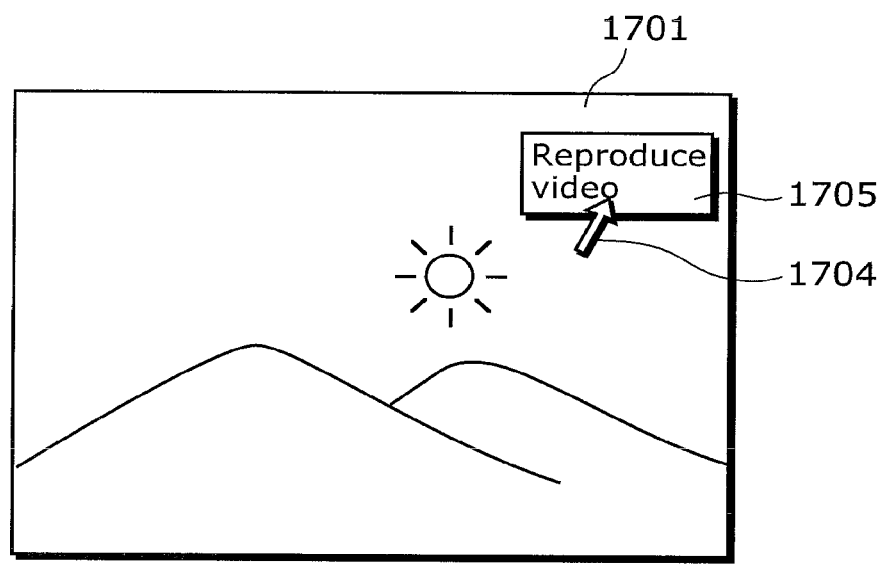
FIG. 24 is a diagram showing an example of an image displayed on a display unit of the head-mounted display according to the fourth embodiment of the present invention.

As shown in FIG. 24, it is assumed that various images are displayed on the display unit 1701, and a mouse pointer 1704 is displayed on such images. To the eye-gaze tracking device 1703, for example, it is possible to apply the eye-gaze tracking device 1 according to the first or second embodiment.

Then, the display control unit 1702 monitors an output signal from the eye-gaze tracking device 1703, and moves the mouse pointer 1704 that is displayed on the display unit 1701, following the movement of the user's gaze. This allows, for example, a processing executing unit (not shown in the figure) to execute processing associated with an icon 1705 (video reproduction processing in the example shown in FIG. 24) pointed by the mouse pointer 1704.

(Fifth Embodiment)

Figure 25:
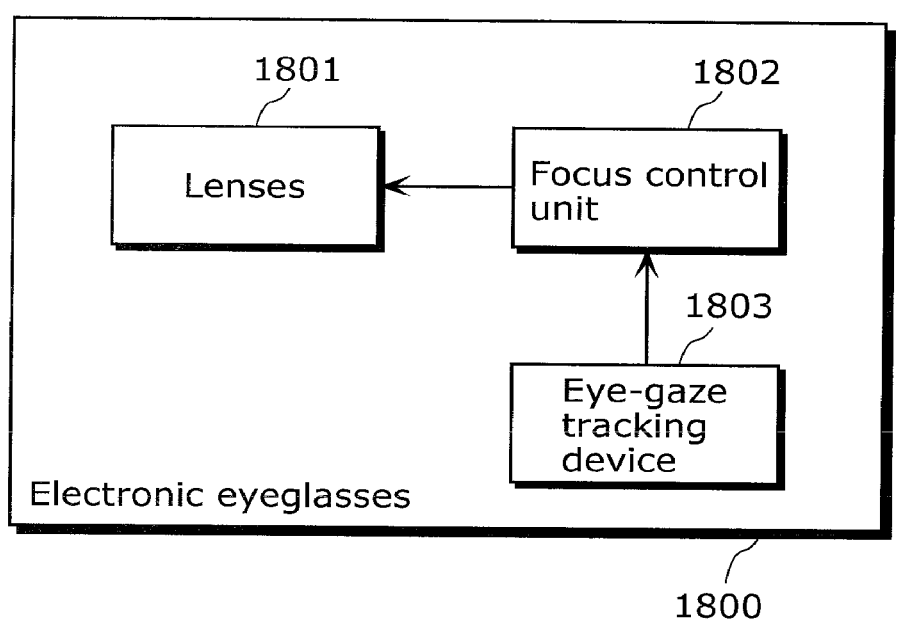
FIG. 25 is a block diagram of electronic eyeglasses according to a fifth embodiment of the present invention.
Figure 26:
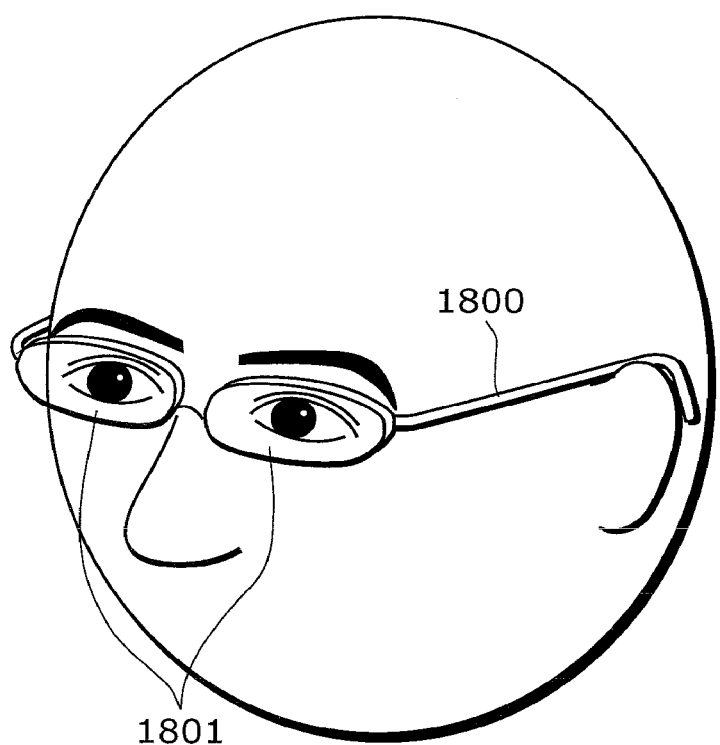
FIG. 26 is a diagram showing a state in which the user is wearing the electronic eyeglasses according to the fifth embodiment of the present invention.

Next, electronic eyeglasses 1800 according to a fifth embodiment of the present invention will be described with reference to FIGS. 25 and 26. The electronic eyeglasses 1800 are eyeglasses capable of changing a focal point of each lens according to the user's gaze position. Specifically, the electronic eyeglasses 1800 include: lenses 1801, a focus control unit 1802, and an eye-gaze tracking device 1803.

Each lens 1801 is located before an eye of the user, and can electronically change the focal point.

To the eye-gaze tracking device 1803, for example, it is possible to apply the eye-gaze tracking device 1 according to the first or second embodiment.

Then, the focus control unit 1802 monitors an output signal from the eye-gaze tracking device 1803, and changes the focal point of each lens 1801, following the movement of the user's gaze. For example, when the user is taking a close look at a book to read or the like, the focus control unit 1802 controls the focal point of each lens 1801 so as to focus each lens 1801 at a closer point. In addition, when the user is looking at a landscape in the distance, the focus control unit 1802 controls the focal point of each lens 1801 so as to focus each lens 1801 at a distant point.

Note that in the present embodiment, it is assumed that the right and left eyes of the user are gazing at the same point. This allows the eye-gaze tracking device 1803 to detect the gaze position from the electro-oculogram.

(Sixth Embodiment)

Figure 27:
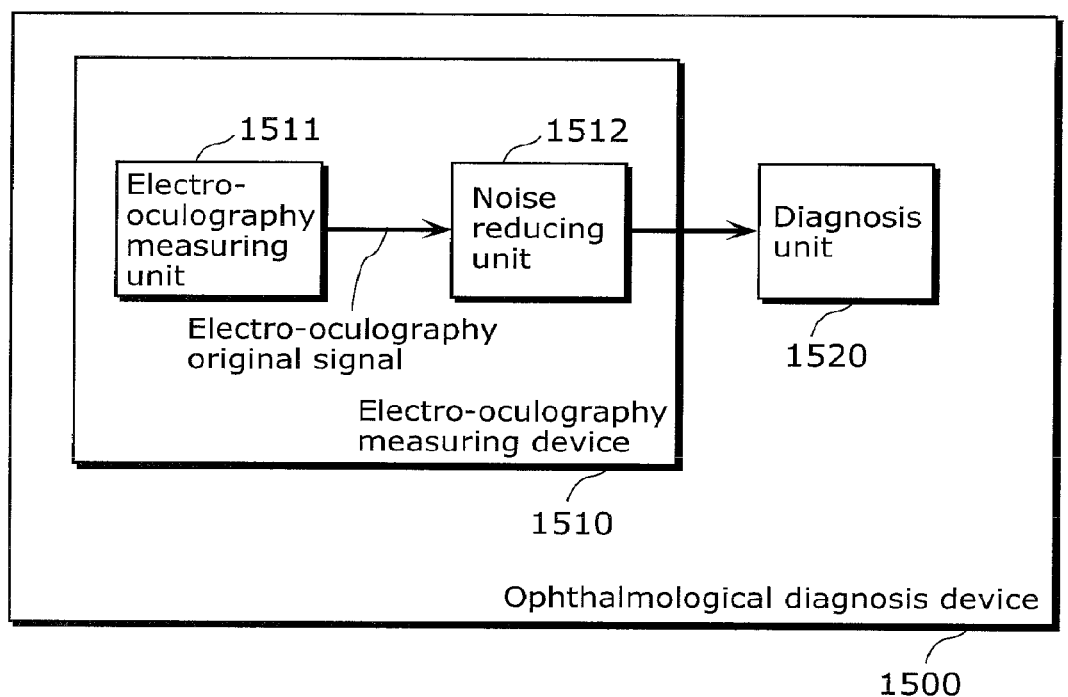
FIG. 27 is a block diagram of an ophthalmological diagnosis device according to a sixth embodiment of the present invention.

Next, an ophthalmological diagnosis device 1500 according to a sixth embodiment of the present invention will be described with reference to FIG. 27. The ophthalmological diagnosis device 1500 diagnoses abnormality of retinal resident potential by measuring an electro-oculogram through electrodes attached around the user's eye. Specifically, the ophthalmological diagnosis device 1500 includes an electro-oculography measuring device 1510 and a diagnosis unit 1520. The electro-oculography measuring device 1510, which is attached around the user's eye, measures the electro-oculogram and includes an electro-oculography measuring unit 1511 which outputs the electro-oculography original signal and a noise reduction unit 1512 which performs noise reduction processing on the electro-oculography original signal.

The diagnosis unit 1520 is considered to calculate, for example, Arden ratio that is a ratio between the electro-oculography signal when the eye is adjusted to brightness and the electro-oculography signal when the eye is adjusted to darkness, so as to diagnose the retinal condition from abnormality of the Arden ratio. To the noise reduction unit 1512 in the electro-oculography measuring device 1510, for example, it is possible to apply the eye-gaze tracking device 1 according to the first embodiment. Specifically, a value obtained by the subtractor 11 subtracting, from the observation voltage v, the drift estimation value $$\hat{\beta} \qquad \text{[Math 51]}$$

may be input into the diagnosis unit 1520.

However, the electro-oculography measuring device 1510 according to the sixth embodiment is not limited to the use described above. For other uses, the electro-oculography measuring device is also applicable to a device which performs turning on and off the switch according to the amount of change in electro-oculogram, or to remote-control operations and so on of mobile devices such as a cellular phone, a music player, and so on.

Note that the present embodiment assumes that electrodes are attached around the user's eye, but any method may be used such as attaching the electrodes around the ear or providing the electrodes in contact with the skin.

(Other Embodiment)

In the embodiments described above, respective blocks may be individually configured into one chip using a semiconductor device such as LSI, or may include one chip so as to include part or all of the blocks. Note that what is referred to as LSI here is also referred to as: IC, system LSI, super LSI, and ultra LSI.

In addition, the circuit integration technique may be realized not only by LSI but also by a dedicated circuit or a general-purpose processor. After manufacturing an LSI, a Field Programmable Gate Array (FPGA) that is programmable or a reconfigurabie processor that allows reconfiguration of connections and settings of circuit cells within the LSI may be used.

Furthermore, when another circuit integration technique appears to replace the LSI as a result of progress in semiconductor technology or another derivative technique, the technique may naturally be used to integrate function blocks. Application of biotechnology and so on is one of the possibilities.

In addition, each process in the above embodiments may be realized using hardware or software. Furthermore, the above embodiments may be realized by mixed processing by software and hardware. Note that it goes without saying that adjustment of timing for performing each process is necessary in the case of realizing, using hardware, the wearable camera according to the above embodiments. In the above embodiments, for convenience of description, details of timing adjustment for different types of signals, which is required in actual hardware designing, are omitted.

In the case of realizing each process in the above embodiments using software, each process is realized by executing a program on a computer having a general configuration such as CPU and RAM. The program like this may be recorded on a non-volatile computer-readable recording medium.

FIG. 28 is a diagram showing essential constituent elements of the eye-gaze tracking device according to the present invention, and when the present invention is realized as an eye-gaze tracking device, the eye gaze tracking device includes the eye-gaze tracking unit 10 and the drift estimating unit 20.

Note that it is also possible to configure the present invention as an electro-oculography measuring device, and in this case, the electro-oculography measuring device includes at least the drift estimating unit 20 and the subtractor 11.

Note that the present invention may also be realized as an eye-gaze tracking method including each processing according to the embodiments described above. This method is typically implemented by a computer or an integrated circuit in which each processing is configured into hardware.

Note that a specific configuration according to the present invention is not limited to the embodiments described above, but may be changed or modified in various ways within the scope not departing from the present invention.

Industrial Applicability

An eye-gaze tracking device according to the present invention is allows detecting a gaze with high accuracy, and it is expected to apply the eye-gaze tracking device as an interface or the like to various devices such as a wearable device (for focus control in a wearable camera, head-mounted display, or electronic eyeglasses). In addition, since an electro-oculography estimating device according to the present invention allows calculating an electro-oculogram with high accuracy, it is possible to apply the electro-oculography estimating device to analysis of the electro-oculogram in the electrophysiological field.

What is claimed is:

1. An eye-gaze tracking device which detects a gaze direction of a user based on an electro-oculogram, said eye-gaze tracking device comprising:
    a drift estimating unit configured to estimate drift noise included in a set of observation voltages among observation voltages that are electro-oculograms generated in a living body and observed at the plurality of electrodes, based on a component outside an electro-oculography subspace that is an assembly of sets of electro-oculograms theoretically observed at a plurality of electrodes; and
    an eye-gaze tracking unit configured to detect the gaze direction of the user, based on a signal generated by removing, from the observation voltages, the drift noise estimated by said drift estimating unit,
    wherein the electro-oculography subspace is obtained by mapping a point in a gaze vector space in accordance with a predetermined electro-oculography conversion function, the point indicating the gaze direction of the user within a predetermined range,
    the electro-oculography conversion function is a nonlinear function, and
    the nonlinear function is a function for calculating a theoretical value of the electro-oculogram generated at an arbitrary three-dimensional spatial position, based on: a right-eye corneal distance and a right-eye retinal distance each of which is a distance to the arbitrary three-dimensional spatial position from a corresponding one of a right eye cornea and a right eye retina; and a left-eye corneal distance and a left-eye retinal distance each of which is a distance to the arbitrary three-dimensional spatial position from a corresponding one of a left eye cornea and a left eye retina.

2. The eye-gaze tracking device according to claim 1, wherein a boundary of the predetermined range is a curve.

3. The eye-gaze tracking device according to claim 2, wherein the boundary of the predetermined range is a curve which is vertically asymmetrical with respect to a horizontal gaze direction of the user.

4. The eye-gaze tracking device according to claim 1, wherein the predetermined range is a range of the gaze direction of the user when the user circularly rotates an eyeball.

5. The eye-gaze tracking device according to claim 4, further comprising
    a function calculating unit configured to calculate the electro-oculography conversion function based on an observation voltage observed at each of the plurality of electrodes for each gaze direction,
    wherein said function calculating unit is configured to estimate the drift noise based on a difference between two observation voltages that are observed at a same point when the user circularly rotates the eyeball two times, and to calculate the electro-oculography conversion function based on a voltage obtained by removing the estimated drift noise from at least one of the two observation voltages.

6. The eye-gaze tracking device according to claim 1, wherein the nonlinear function includes predetermined coefficients each of which is individually settable for a corresponding one of the right-eye corneal distance, the right-eye retinal distance, the left-eye corneal distance, and the left-eye retinal distance.

7. The eye-gaze tracking device according to claim 5, wherein said function calculating unit is configured to calculate the nonlinear function by interpolating the electro-oculogram in a gaze direction in which no voltage is observed, using each of the observation voltages observed at each of the plurality of electrodes for each gaze direction.

8. The eye-gaze tracking device according to claim 1, wherein, when, at time t, N observation voltages are $V_i(t)$ (i=1,...N), and a drift estimation value of the drift noise included in each of the N observation voltages is $$\hat{\beta}_i(t) \qquad \text{[Math 1]}$$

and when the electro-oculography conversion function corresponding to each of the N observation voltages is $eog_i()$ and the gaze position of the user is θ(t), said eye-gaze tracking unit is configured to estimate, so as to derive a smallest value in accordance with $$\sum_{i=1}^{N} \left(v_i(t) - \left(eog_i(\theta(t)) + \hat{\beta}_i(t)\right)\right)^2,\quad \text{[Math 2]}$$

a gaze estimation value $$\hat{\theta}(t) \quad \text{[Math 3]}$$

which is an estimation value of the gaze position θ(t) of the user, and when a residual difference at the time of estimating the gaze estimation value detected by said eye-gaze tracking unit is $$\hat{\epsilon}_i(t) = v_i(t) - (eog_i(\theta(t)) + \hat{\beta}_i(t)) \quad \text{[Math 4]}$$

said drift estimating unit is configured to estimate the drift estimation value in accordance with:

$$\hat{\beta}_i(t) = \hat{\beta}_i(t-\Delta t) + \hat{\epsilon}_i(t-\Delta t) \quad \text{[Math 5]}.$$

9. The eye-gaze tracking device according to claim 8, wherein said drift estimating unit is further configured to perform low-pass filtering on the residual difference and estimate the drift estimation value from the residual difference on which the low-pass filtering has been performed.

10. The eye-gaze tracking device according to claim 9, wherein said drift estimating unit is configured to increase a cutoff frequency for the low-pass filtering when the gaze estimation value exceeds the boundary of the predetermined range.

11. The eye-gaze tracking device according to claim 9, further comprising
a saccade detecting unit configured to detect, from the observation voltages, an occurrence of saccadic movement that is rapid eyeball movement,
wherein said drift estimating unit is configured to decrease the cutoff frequency for the low-pass filtering when said saccade detecting unit detects the occurrence of the saccadic movement.

12. The eye-gaze tracking device according to claim 11, wherein said saccade detecting unit includes:
a delayed signal generating unit configured to output a delayed signal by delaying each of the observation voltages for a predetermined delay time; and
a subtraction unit configured to generate an output signal by subtracting the delayed signal from the each of the observation voltages,
wherein said saccade detecting unit is configured to determine a signal above a predetermined threshold as a saccade signal indicating saccadic movement, the signal being included in the output signal, and
the predetermined delay time is shorter than a single fixation time of the user.

13. A wearable camera which captures an image in a gaze direction of a user, said wearable camera comprising:
an imaging unit;
the eye-gaze tracking device according to claim 1; and
an imaging control unit configured to cause said imaging unit to capture the image in the gaze direction detected by said eye-gaze tracking device.

14. A head-mounted display which moves a mouse pointer in a gaze direction of a user, said head-mounted display comprising:

a display unit configured to display an image and the mouse pointer;
the eye-gaze tracking device according to claim 1; and
a display control unit configured to move the mouse pointer in the gaze direction detected by said eye-gaze tracking device, the mouse pointer being displayed on the display unit.

15. Electronic eyeglasses which change a focal point of each of lenses according to a gaze position of a user, said electronic eyeglasses comprising:
lenses each having a changeable focal point;
eye-gaze tracking device according to claim 1; and
a focus control unit configured to change the focal point of each of said lenses according to the gaze position detected by said eye-gaze tracking device.

16. An ophthalmological diagnosis device which diagnoses a retinal state of a user, said ophthalmological diagnosis device comprising:
the eye-gaze tracking device according to claim 1; and
a diagnosis unit configured to detect retinal abnormality of the user, based on the signal obtained by removing, from the observation voltages, the drift noise estimated by the drift estimating unit.

17. An eye-gaze tracking method for detecting a gaze direction of a user based on an electro-oculogram, said eye-gaze tracking method comprising:
estimating drift noise included in a set of observation voltages among the observation voltages that are the electro-oculograms generated in a living body and observed at the plurality of electrodes, based on a component outside an electro-oculography subspace that is an assembly of sets of electro-oculograms theoretically observed at a plurality of electrodes; and
detecting the gaze direction of the user, based on a signal generated by removing, from the observation voltages, the drift noise estimated in said estimating,
wherein the electro-oculography subspace is obtained by mapping a point in a gaze vector space in accordance with a predetermined electro-oculography conversion function, the point indicating the gaze direction of the user within a predetermined range,
the electro-oculography conversion function is a nonlinear function, and
the nonlinear function is a function for calculating a theoretical value of the electro-oculogram generated at an arbitrary three-dimensional spatial position, based on: a right-eye corneal distance and a right-eye retinal distance each of which is a distance to the arbitrary three-dimensional spatial position from a corresponding one of a right eye cornea and a right eye retina; and a left-eye corneal distance and a left-eye retinal distance each of which is a distance to the arbitrary three-dimensional spatial position from a corresponding one of a left eye cornea and a left eye retina.

18. An electro-oculography measuring device which measures an electro-oculogram of a user, said electro-oculography measuring device comprising:
a drift estimating unit configured to estimate drift noise included in a set of observation voltages, based on a component outside an electro-oculography subspace that is an assembly of sets of electro-oculograms theoretically observed at a plurality of electrodes, the observation voltages being electro-oculograms generated in a living body and observed at the plurality of electrodes; and a subtractor which subtracts the drift noise estimated by said drift estimating device, based on the observation voltages, wherein the electro-oculography subspace is obtained by mapping a point in a gaze vector space in accordance with a predetermined electro-oculography conversion function, the point indicating a gaze direction of the user within a predetermined range, the electro-oculography conversion function is a nonlinear function, and the nonlinear function is a function for calculating a theoretical value of the electro-oculogram generated at an arbitrary three-dimensional spatial position, based on: a right-eye corneal distance and a right-eye retinal distance each of which is a distance to the arbitrary three-dimensional spatial position from a corresponding one of a right eye cornea and a right eye retina; and a left-eye corneal distance and a left-eye retinal distance each of which is a distance to the arbitrary three-dimensional spatial position from a corresponding one of a left eye cornea and a left eye retina.

19. A non-transitory computer-readable medium having a program stored thereon for detecting a gaze direction of a user based on an electro-oculogram, said program causing a computer to execute:

estimating drift noise included in a set of observation voltages among the observation voltages that are the electro-oculograms generated in a living body and observed at the plurality of electrodes, based on a component outside an electro-oculography subspace that is an assembly of sets of electro-oculograms theoretically observed at a plurality of electrodes; and detecting the gaze direction of the user, based on a signal generated by removing, from the observation voltages, the drift noise estimated in the estimating, wherein the electro-oculography subspace is obtained by mapping a point in a gaze vector space in accordance with a predetermined electro-oculography conversion function, the point indicating the gaze direction of the user within a predetermined range, the electro-oculography conversion function is a nonlinear function, and the nonlinear function is a function for calculating a theoretical value of the electro-oculogram generated at an arbitrary three-dimensional spatial position, based on: a right-eye corneal distance and a right-eye retinal distance each of which is a distance to the arbitrary three-dimensional spatial position from a corresponding one of a right eye cornea and a right eye retina; and a left-eye corneal distance and a left-eye retinal distance each of which is a distance to the arbitrary three-dimensional spatial position from a corresponding one of a left eye cornea and a left eye retina.

\* \* \* \* \*